US008765416B2

(12) United States Patent
Shibuya et al.

(10) Patent No.: US 8,765,416 B2
(45) Date of Patent: Jul. 1, 2014

(54) PARTICULATE COMPOSITION CONTAINING ANHYDROUS CRYSTALLINE 2-O-ALPHA-D-GLUCOSYL-L-ASCORBIC ACID, PROCESS FOR PRODUCING THE SAME, AND USES THEREOF

(75) Inventors: Takashi Shibuya, Okayama (JP);
Seisuke Izawa, Okayama (JP);
Tomoyuki Nishimoto, Okayama (JP);
Shigeharu Fukuda, Okayama (JP);
Toshio Miyake, Okayama (JP)

(73) Assignee: Hayashibara Co., Ltd., Okayama-Shi, Okayama (JP)

( * ) Notice: Subject to any disclaimer, the term of this patent is extended or adjusted under 35 U.S.C. 154(b) by 477 days.

(21) Appl. No.: 12/875,786

(22) Filed: Sep. 3, 2010

(65) Prior Publication Data
US 2011/0091726 A1   Apr. 21, 2011

(30) Foreign Application Priority Data

Sep. 3, 2009 (JP) ................ 2009/204142
Dec. 28, 2009 (JP) ................ 2009/298857
May 21, 2010 (JP) ................ 2010/117835
Aug. 26, 2010 (JP) ................ 2010/190139

(51) Int. Cl.
*C12P 19/44* (2006.01)
(52) U.S. Cl.
USPC ............. 435/74; 536/123.1; 536/123.13
(58) Field of Classification Search
None
See application file for complete search history.

(56) References Cited

U.S. PATENT DOCUMENTS

| 5,137,723 A * | 8/1992 | Yamamoto et al. ......... 424/400 |
| 5,407,812 A * | 4/1995 | Sakai et al. ............... 435/75 |
| 5,468,850 A * | 11/1995 | Mandai et al. .............. 536/18.5 |
| 6,777,215 B2 * | 8/2004 | Andersen et al. ........... 435/193 |
| 2007/0148287 A1 * | 6/2007 | Svendsen et al. ........... 426/20 |

FOREIGN PATENT DOCUMENTS

| EP | 0 425 066 A1 | 5/1991 |
| EP | 1 553 186 A1 | 7/2005 |
| JP | S50-63189 | 5/1975 |
| JP | S63-039597 | 2/1988 |
| JP | 3135992 A | 6/1991 |
| JP | 3139288 A | 6/1991 |
| JP | 3183492 A | 8/1991 |
| JP | 4046112 A | 2/1992 |
| JP | 4182412 A | 6/1992 |
| JP | 4182413 A | 6/1992 |
| JP | 4182414 A | 6/1992 |
| JP | 4182415 A | 6/1992 |
| JP | 4182419 A | 6/1992 |
| JP | 5117290 A | 5/1993 |
| JP | 5208991 A | 8/1993 |
| JP | H05-244945 | 9/1993 |
| JP | 8333260 A | 12/1996 |
| JP | 2002088095 A | 3/2002 |
| JP | 2002326924 A | 11/2002 |
| JP | 2003171290 A | 6/2003 |
| JP | 2004065098 A | 3/2004 |
| JP | 2004217597 A | 8/2004 |
| JP | 2005239653 A | 9/2005 |
| JP | 2006225327 A | 8/2006 |
| JP | 2007063177 A | 3/2007 |
| WO | 01/90338 A1 | 11/2001 |
| WO | 02/10361 A1 | 2/2002 |
| WO | 2005/034938 A1 | 4/2005 |
| WO | 2005/087182 A1 | 9/2005 |
| WO | 2006/033412 A1 | 3/2006 |
| WO | 2006022174 A1 | 3/2006 |
| WO | 2006/132310 A1 | 12/2006 |
| WO | 2006/137129 A1 | 12/2006 |
| WO | 2007/086327 A1 | 8/2007 |

OTHER PUBLICATIONS

Tanaka et al., "Characterization of *Bacillus stearothermophilus* cyclodextrin glucanotransferase in ascorbic acid 2-O-a-glucoside formation." (1991), Biochemica et Biophysica Acta, 1078: 127-132.*

Rendleman, Jr., "The Production of Cyclodextrins using CGTase from *Bacillus macerans*." (1997), Methods in Biotechnology, vol. 10: Carbohydrate Biotechnology Protocols, 89-101.*

Kelly et al. "The evolution of cyclodextrin glucanotransferase product specificity" (2009) Applied Microbiology Biotechnology, vol. 84: 119-133.*

Search Report dated Dec. 22, 2010 from the European Patent Office issued in Appl. No. EP 10175307.7.

Mandai, T. et al., "The Crystal Structure and Physicochemical Properties of L-ascorbic acid 2-glucoside", Carbohydrate Research, vol. 232, (1992), pp. 197-205.

Inoue, Y. et al., "Application of Ascorbic Acid 2-Glucoside as a Solubilizing Agent for Clarithromycin: Solubilization and Nanoparticle Formation", International Journal of Pharmaceutics, vol. 331, (2007), pp. 38-45.

(Continued)

*Primary Examiner* — Jon P Weber
*Assistant Examiner* — Teresa E Knight
(74) *Attorney, Agent, or Firm* — Browdy and Neimark, PLLC

(57) ABSTRACT

The present invention aims to provide a particulate composition containing anhydrous crystalline 2-O-α-D-glucosyl-L-ascorbic acid having a significantly, hardly solidifiable property compared to conventional ones in a grade for use in quasi-drugs; a process for producing the same; and uses thereof. The present invention solves the above object by providing a particulate composition containing anhydrous crystalline 2-O-α-D-glucosyl-L-ascorbic in an amount of over 98.0% by weight but less than 99.9% by weight, on a dry solid basis; or a degree of crystallinity of 90% or higher for anhydrous crystalline 2-O-α-D-glucosyl-L-ascorbic acid; and by providing a process for producing the same and uses thereof.

5 Claims, 5 Drawing Sheets

(56) References Cited

OTHER PUBLICATIONS

Hermans, P.H. et al. "Quantitative X-ray investigations on the Crystallinity of Cellulose Fibers", Journal of Applied Physics, vol. 19, (1948), pp. 491-506.

Hermans, P.H. et al. "X-ray Studies on the Chrystallinity of Cellulose", Journal of Applied Physics, vol. 4, (1949), pp. 135-144.

Bunya, "Development of Stable Vitamin C and its Applications," San-yo Gijutsu Zassi (山陽技術雑誌), 45(1): 63-69 (1997).

Wako Analytical Circle, No. 29, p. 6 (2003).

Markosyan, et al "Transglycosylation of L-Ascorbic Acid," Applied Biochemistry and Microbiology, 43(1): 36-40 (2007).

Aga, et al "Synthesis of 2-O-alpha-D-Glucopyranosyl L-Ascorbic Acid by Cyclomaltodextrin Glucanotransferase from *Bacillus stearothermophilus*", Agric. Biol. Chem. 55(7): 1751-1756 (1991).

\* cited by examiner

SEQUENCE LISTING

```
<160> NUMBER OF SEQ ID NOS: 2

<210> SEQ ID NO 1
<211> LENGTH: 680
<212> TYPE: PRT
<213> ORGANISM: Geobacillus stearothermophilus

<400> SEQUENCE: 1

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60

Asp Met Gly Val Thr Ala Ile Trp Ile Ser Gln Pro Val Glu Asn Val
65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
    130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
    210                 215                 220

Asp Ala Val Lys His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
                245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
        275                 280                 285

Leu Arg Asn Asn Ser Asp Asn Trp Tyr Gly Phe Asn Gln Met Ile Gln
    290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
                325                 330                 335

Lys Val Asp Met Ala Leu Ala Val Leu Leu Thr Ser Arg Gly Val Pro
```

```
                     340                 345                 350
Asn Ile Tyr Tyr Gly Thr Glu Gln Tyr Met Thr Gly Asn Gly Asp Pro
                355                 360                 365
Asn Asn Arg Lys Met Met Ser Ser Phe Asn Lys Asn Thr Arg Ala Tyr
            370                 375                 380
Gln Val Ile Gln Lys Leu Ser Ser Leu Arg Arg Asn Asn Pro Ala Leu
385                 390                 395                 400
Ala Tyr Gly Asp Thr Glu Gln Arg Trp Ile Asn Gly Asp Val Tyr Val
                405                 410                 415
Tyr Glu Arg Gln Phe Gly Lys Asp Val Val Leu Val Ala Val Asn Arg
            420                 425                 430
Ser Ser Ser Ser Asn Tyr Ser Ile Thr Gly Leu Phe Thr Ala Leu Pro
        435                 440                 445
Ala Gly Thr Tyr Thr Asp Gln Leu Gly Gly Leu Asp Gly Asn Thr
        450                 455                 460
Ile Gln Val Gly Ser Asn Gly Ser Val Asn Ala Phe Asp Leu Gly Pro
465                 470                 475                 480
Gly Glu Val Gly Val Trp Ala Tyr Ser Ala Thr Glu Ser Thr Pro Ile
                485                 490                 495
Ile Gly His Val Gly Pro Met Met Gly Gln Val Gly His Gln Val Thr
            500                 505                 510
Ile Asp Gly Glu Gly Phe Gly Thr Asn Thr Gly Thr Val Lys Phe Gly
        515                 520                 525
Thr Thr Ala Ala Asn Val Val Ser Trp Ser Asn Asn Gln Ile Val Val
        530                 535                 540
Ala Val Pro Asn Val Ser Pro Gly Lys Tyr Asn Ile Thr Val Gln Ser
545                 550                 555                 560
Ser Ser Gly Gln Thr Ser Ala Ala Tyr Asp Asn Phe Glu Val Leu Thr
                565                 570                 575
Asn Asp Gln Val Ser Val Arg Phe Val Val Asn Asn Ala Thr Thr Asn
            580                 585                 590
Leu Gly Gln Asn Ile Tyr Ile Val Gly Asn Val Tyr Glu Leu Gly Asn
        595                 600                 605
Trp Asp Thr Ser Lys Ala Ile Gly Pro Met Phe Asn Gln Val Val Tyr
        610                 615                 620
Ser Tyr Pro Thr Trp Tyr Ile Asp Val Ser Val Pro Glu Gly Lys Thr
625                 630                 635                 640
Ile Glu Phe Lys Phe Ile Lys Lys Asp Ser Gln Gly Asn Val Thr Trp
                645                 650                 655
Glu Ser Gly Ser Asn His Val Tyr Thr Thr Pro Thr Asn Thr Thr Gly
            660                 665                 670
Lys Ile Ile Val Asp Trp Gln Asn
        675                 680

<210> SEQ ID NO 2
<211> LENGTH: 2133
<212> TYPE: DNA
<213> ORGANISM: Geobacillus stearothermophilus

<400> SEQUENCE: 2 atg aga aga tgg ctt tcg cta gtc ttg agc atg tca ttt gta ttt agt    48
Met Arg Arg Trp Leu Ser Leu Val Leu Ser Met Ser Phe Val Phe Ser
  1               5                  10                  15 gca att ttt ata gta tct gat acg cag aaa gtc acc gtt gaa gca gct    96
Ala Ile Phe Ile Val Ser Asp Thr Gln Lys Val Thr Val Glu Ala Ala
```

|   |   |   |
|---|---|---|
| | 20 25 30 | |
| gga aat ctt aat aag gta aac ttt aca tca gat gtt gtc tat caa att<br>Gly Asn Leu Asn Lys Val Asn Phe Thr Ser Asp Val Val Tyr Gln Ile<br>35 40 45 | 144 |
| gta gtg gat cga ttt gtg gat gga aat aca tcc aat aat ccg agt gga<br>Val Val Asp Arg Phe Val Asp Gly Asn Thr Ser Asn Asn Pro Ser Gly<br>50 55 60 | 192 |
| gca tta ttt agc tca gga tgt acg aat tta cgc aag tat tgc ggt gga<br>Ala Leu Phe Ser Ser Gly Cys Thr Asn Leu Arg Lys Tyr Cys Gly Gly<br>65 70 75 80 | 240 |
| gat tgg caa ggc atc atc aat aaa att aac gat ggg tat tta aca gat<br>Asp Trp Gln Gly Ile Ile Asn Lys Ile Asn Asp Gly Tyr Leu Thr Asp<br>85 90 95 | 288 |
| atg ggt gtg aca gcg ata tgg att tct cag cct gta gaa aat gta ttt<br>Met Gly Val Thr Ala Ile Trp Ile Ser Gln Pro Val Glu Asn Val Phe<br>100 105 110 | 336 |
| tct gtg atg aat gat gca agc ggt tca gcc tcc tat cat ggt tat tgg<br>Ser Val Met Asn Asp Ala Ser Gly Ser Ala Ser Tyr His Gly Tyr Trp<br>115 120 125 | 384 |
| gcg cgc gat ttc aaa aag cca aac ccg ttt ttt ggt acc ctc agt gat<br>Ala Arg Asp Phe Lys Lys Pro Asn Pro Phe Phe Gly Thr Leu Ser Asp<br>130 135 140 | 432 |
| ttc caa cgt tta gtt gat gcc gca cat gca aaa gga ata aag gta att<br>Phe Gln Arg Leu Val Asp Ala Ala His Ala Lys Gly Ile Lys Val Ile<br>145 150 155 160 | 480 |
| att gac ttt gcc ccc aac cat act tct cct gct tca gaa acg aat cct<br>Ile Asp Phe Ala Pro Asn His Thr Ser Pro Ala Ser Glu Thr Asn Pro<br>165 170 175 | 528 |
| tct tat atg gaa aac gga cga ctg tac gat aat ggg aca ttg ctt ggc<br>Ser Tyr Met Glu Asn Gly Arg Leu Tyr Asp Asn Gly Thr Leu Leu Gly<br>180 185 190 | 576 |
| ggt tac aca aat gat gcc aac atg tat ttt cac cat aac ggt gga aca<br>Gly Tyr Thr Asn Asp Ala Asn Met Tyr Phe His His Asn Gly Gly Thr<br>195 200 205 | 624 |
| acg ttt tcc agc tta gag gat ggg att tat cga aat ctg ttt gac ttg<br>Thr Phe Ser Ser Leu Glu Asp Gly Ile Tyr Arg Asn Leu Phe Asp Leu<br>210 215 220 | 672 |
| gcg gac ctt aac cat cag aac cct gtt att gat agg tat tta aaa gat<br>Ala Asp Leu Asn His Gln Asn Pro Val Ile Asp Arg Tyr Leu Lys Asp<br>225 230 235 240 | 720 |
| gca gta aaa atg tgg ata gat atg ggg att gat ggt atc cgt atg gat<br>Ala Val Lys Met Trp Ile Asp Met Gly Ile Asp Gly Ile Arg Met Asp<br>245 250 255 | 768 |
| gcg gtg aag cac atg ccg ttt gga tgg caa aaa tct ctg atg gat gag<br>Ala Val Lys His Met Pro Phe Gly Trp Gln Lys Ser Leu Met Asp Glu<br>260 265 270 | 816 |
| att gat aac tat cgt cct gtc ttt acg ttt ggg gag tgg ttt ttg tca<br>Ile Asp Asn Tyr Arg Pro Val Phe Thr Phe Gly Glu Trp Phe Leu Ser<br>275 280 285 | 864 |
| gaa aat gaa gtg gac gcg aac aat cat tac ttt gcc aat gaa agt gga<br>Glu Asn Glu Val Asp Ala Asn Asn His Tyr Phe Ala Asn Glu Ser Gly<br>290 295 300 | 912 |
| atg agt ttg ctc gat ttt cgt ttc gga caa aag ctt cgt caa gta ttg<br>Met Ser Leu Leu Asp Phe Arg Phe Gly Gln Lys Leu Arg Gln Val Leu<br>305 310 315 320 | 960 |
| cgc aat aac agc gat aat tgg tat ggc ttt aat caa atg att caa gat<br>Arg Asn Asn Ser Asp Asn Trp Tyr Gly Phe Asn Gln Met Ile Gln Asp<br>325 330 335 | 1008 |
| acg gca tca gca tat gac gag gtt ctc gat caa gta aca ttc ata gac | 1056 |

```
Thr Ala Ser Ala Tyr Asp Glu Val Leu Asp Gln Val Thr Phe Ile Asp
            340                 345                 350 aac cat gat atg gat cgg ttt atg att gac gga gga gat ccg cgc aag      1104
Asn His Asp Met Asp Arg Phe Met Ile Asp Gly Gly Asp Pro Arg Lys
            355                 360                 365 gtg gat atg gca ctt gct gta tta ttg aca tcc cgt ggc gta ccg aat      1152
Val Asp Met Ala Leu Ala Val Leu Leu Thr Ser Arg Gly Val Pro Asn
        370                 375                 380 att tac tat ggt aca gag caa tac atg acc ggt aac ggc gat cca aac      1200
Ile Tyr Tyr Gly Thr Glu Gln Tyr Met Thr Gly Asn Gly Asp Pro Asn
385                 390                 395                 400 aat cgt aag atg atg agt tca ttc aat aaa aat act cgc gcg tat caa      1248
Asn Arg Lys Met Met Ser Ser Phe Asn Lys Asn Thr Arg Ala Tyr Gln
                405                 410                 415 gtg att caa aaa cta tct tct ctc cga cga aac aat ccg gcg tta gct      1296
Val Ile Gln Lys Leu Ser Ser Leu Arg Arg Asn Asn Pro Ala Leu Ala
            420                 425                 430 tat ggt gat acc gaa cag cgt tgg atc aat ggc gat gtg tat gtg tat      1344
Tyr Gly Asp Thr Glu Gln Arg Trp Ile Asn Gly Asp Val Tyr Val Tyr
        435                 440                 445 gag cga cag ttt ggc aaa gat gtt gtg tta gtt gcc gtt aat cgt agt      1392
Glu Arg Gln Phe Gly Lys Asp Val Val Leu Val Ala Val Asn Arg Ser
    450                 455                 460 tca agc agt aat tac tcg att act ggc tta ttt aca gct tta cca gca      1440
Ser Ser Ser Asn Tyr Ser Ile Thr Gly Leu Phe Thr Ala Leu Pro Ala
465                 470                 475                 480 gga aca tat acg gat cag ctt ggc ggt ctt tta gac gga aat aca att      1488
Gly Thr Tyr Thr Asp Gln Leu Gly Gly Leu Leu Asp Gly Asn Thr Ile
                485                 490                 495 caa gtc ggt tca aat gga tca gtt aat gca ttt gac tta gga ccg ggg      1536
Gln Val Gly Ser Asn Gly Ser Val Asn Ala Phe Asp Leu Gly Pro Gly
            500                 505                 510 gaa gtc ggt gta tgg gca tac agt gca aca gaa agc acg cca att att      1584
Glu Val Gly Val Trp Ala Tyr Ser Ala Thr Glu Ser Thr Pro Ile Ile
        515                 520                 525 ggt cat gtt gga ccg atg atg ggg caa gtc ggt cat caa gta acc att      1632
Gly His Val Gly Pro Met Met Gly Gln Val Gly His Gln Val Thr Ile
    530                 535                 540 gat ggc gaa gga ttc gga aca aat acg ggc act gtg aag ttc gga acg      1680
Asp Gly Glu Gly Phe Gly Thr Asn Thr Gly Thr Val Lys Phe Gly Thr
545                 550                 555                 560 aca gct gcc aat gtt gtg tct tgg tct aac aat caa atc gtt gtg gct      1728
Thr Ala Ala Asn Val Val Ser Trp Ser Asn Asn Gln Ile Val Val Ala
                565                 570                 575 gta cca aat gtg tca cca gga aaa tat aat att acc gtc caa tca tca      1776
Val Pro Asn Val Ser Pro Gly Lys Tyr Asn Ile Thr Val Gln Ser Ser
            580                 585                 590 agc ggt caa acg agt gcg gct tat gat aac ttt gaa gta cta aca aat      1824
Ser Gly Gln Thr Ser Ala Ala Tyr Asp Asn Phe Glu Val Leu Thr Asn
        595                 600                 605 gat caa gtg tca gtg cgg ttt gtt gtt aat aac gcg act acc aat cta      1872
Asp Gln Val Ser Val Arg Phe Val Val Asn Asn Ala Thr Thr Asn Leu
    610                 615                 620 ggg caa aat ata tac att gtt ggc aac gta tat gag ctc ggc aac tgg      1920
Gly Gln Asn Ile Tyr Ile Val Gly Asn Val Tyr Glu Leu Gly Asn Trp
625                 630                 635                 640 gac act agt aag gca atc ggt cca atg ttc aat caa gtg gtt tac tcc      1968
Asp Thr Ser Lys Ala Ile Gly Pro Met Phe Asn Gln Val Val Tyr Ser
                645                 650                 655
```

-continued

| | | | | | | | | | | | | | | | | |
|---|---|---|---|---|---|---|---|---|---|---|---|---|---|---|---|---|
| tat | cct | aca | tgg | tat | ata | gat | gtc | agt | gtc | cca | gaa | gga | aag | aca | att | 2016 |
| Tyr | Pro | Thr | Trp | Tyr | Ile | Asp | Val | Ser | Val | Pro | Glu | Gly | Lys | Thr | Ile | |
| | | | 660 | | | | | 665 | | | | | 670 | | | |
| gag | ttt | aag | ttt | att | aaa | aaa | gac | agc | caa | ggt | aat | gtc | act | tgg | gaa | 2064 |
| Glu | Phe | Lys | Phe | Ile | Lys | Lys | Asp | Ser | Gln | Gly | Asn | Val | Thr | Trp | Glu | |
| | | 675 | | | | | 680 | | | | | 685 | | | | |
| agt | ggt | tca | aat | cat | gtt | tat | acg | aca | cca | acg | aat | aca | acc | gga | aaa | 2112 |
| Ser | Gly | Ser | Asn | His | Val | Tyr | Thr | Thr | Pro | Thr | Asn | Thr | Thr | Gly | Lys | |
| | 690 | | | | | 695 | | | | | 700 | | | | | |
| att | ata | gtg | gat | tgg | cag | aac | | | | | | | | | | 2133 |
| Ile | Ile | Val | Asp | Trp | Gln | Asn | | | | | | | | | | |
| 705 | | | | | 710 | | | | | | | | | | | |

PARTICULATE COMPOSITION CONTAINING ANHYDROUS CRYSTALLINE 2-O-ALPHA-D-GLUCOSYL-L-ASCORBIC ACID, PROCESS FOR PRODUCING THE SAME, AND USES THEREOF

BACKGROUND OF THE INVENTION

1. Field of the Invention

The present invention relates to a particulate composition containing anhydrous crystalline 2-O-α-D-glucosyl-L-ascorbic acid, process for producing the same, and uses thereof, more particularly, to a hardly solidifiable particulate composition containing anhydrous crystalline 2-O-α-D-glucosyl-L-ascorbic acid, process for producing the same, and uses thereof as a material for food products, cosmetics, quasi-drugs, and pharmaceuticals.

2. Description of the Prior Art

Due to its advantageous physiological activities and anti-oxidant action, L-ascorbic acid has been used for various purposes, including those for food products and cosmetics. L-Ascorbic acid, however, is unstable because of its direct reducibility and is susceptible to receive oxidative degradation and to lose its physiological activity as the crucial defect. To overcome the defect, the present applicant, as one of the co-applicants of Patent Literature 1, disclosed 2-O-α-D-glucosyl-L-ascorbic acid that is composed of one molecule of D-glucose bound to the hydroxyl group at the C-2 position of L-ascorbic acid (hereinafter, abbreviated as "ascorbic acid 2-glucoside", throughout the specification). As outstanding characteristics, ascorbic acid 2-glucoside does not exhibit direct reducibility but has a satisfactory stability, and it exerts the physiological activities inherent to L-ascorbic acid after being decomposed in living bodies into L-ascorbic acid and D-glucose by an in vivo enzyme inherently existing in the living bodies. According to the process disclosed in Patent Literature 1, ascorbic acid 2-glucoside is formed by allowing a saccharide-transferring enzyme such as cyclomaltodextrin glucanotransferase (abbreviated as "CGTase", hereinafter) or α-glucosidase to act on a solution containing L-ascorbic acid and α-glucosyl saccharide compound.

In Patent Literature 2, the present applicant succeeded in crystallizing ascorbic acid 2-glucoside from a saturated solution of ascorbic acid 2-glucoside and disclosed crystalline ascorbic acid 2-glucoside and a particulate composition containing the same. Until now, crystalline ascorbic acid 2-glucoside has been known to merely exist in an anhydrous crystalline form. Non-Patent Literatures 1 and 2 reported data on X-ray structure analysis for crystalline ascorbic acid 2-glucoside.

In Patent Literatures 3 and 4, the same applicant as the present invention disclosed a process for collecting a high ascorbic acid 2-glucoside content fraction, comprising subjecting a solution containing ascorbic acid 2-glucoside formed by an enzymatic reaction to column chromatography using a strong-acid cation exchange resin, and collecting the fraction. In Patent Literature 5, the same applicant disclosed a process for producing a high ascorbic acid 2-glucoside content product, comprising subjecting a solution containing ascorbic acid 2-glucoside formed by an enzymatic reaction to electrodialysis using an anion-exchange membrane to remove impurities such as L-ascorbic acid and saccharides from the solution; and in Patent Literature 6, the same applicant disclosed a process for producing a high ascorbic acid 2-glucoside content product, comprising subjecting a solution containing ascorbic acid 2-glucoside to an anion-exchange resin and selectively desorbing the ingredients adsorbed on the resin to obtain a fraction rich in ascorbic acid 2-glucoside.

In Patent Literature 7, the same applicant as the present invention disclosed a process for producing ascorbic acid 2-glucoside, comprising allowing α-isomaltosyl glucosaccharide-forming enzyme or α-isomaltosyl glucosaccharide-forming enzyme in combination with CGTase to act on a solution containing L-ascorbic acid and α-glucosyl saccharide compound to form ascorbic acid 2-glucoside. Patent Literatures 8 and 9 applied for by the same applicant as the present invention disclose that α-isomaltosyl glucosaccharide-forming enzyme and α-isomaltosyl-transferring enzyme catalyze saccharide transferring to L-ascorbic acid to form ascorbic acid 2-glucoside.

Referring to uses of ascorbic acid 2-glucoside, many proposals have been made as shown in, for example, Patent Literatures 10 to 29. Depending on its advantageous characteristics, ascorbic acid 2-glucoside has been conventionally used as a material for food products, cosmetics, quasi-drugs, or pharmaceuticals; and it has been extensively used in other uses where L-ascorbic acid could not be used due to its instability, to say nothing of conventional uses of L-ascorbic acid.

As described above, ascorbic acid 2-glucoside is now known to be produced by using L-ascorbic acid and amylaceous substances as materials and various saccharide-transferring enzymes. According to the findings already obtained by the present applicant so far, the method for allowing CGTase as a saccharide-transferring enzyme to act on a solution containing L-ascorbic acid and amylaceous substance is an industrially advantageous method because of its highest production yield of ascorbic acid 2-glucoside. Based on this finding, the present applicant has been producing particulate compositions containing anhydrous crystalline ascorbic acid 2-glucoside by the method of allowing CGTase to act on a solution containing L-ascorbic acid and amylaceous substance, and commercializing the particulate compositions as materials for cosmetics/quasi-drugs and for food products, which are respectively commercialized as "AA2G" and "ASCOFRESH", product names of such particulate compositions and commercialized by Hayashibara Biochemical Laboratories, Inc., Okayama, Japan, and Hayashibara Shoji Inc., Okayama, Japan, respectively (these conventional particulate compositions containing anhydrous crystalline ascorbic acid 2-glucoside that have been commercialized as materials for cosmetics/quasi-drugs and for food products are abbreviated as "quasi-drug grade powders", hereinafter.)

Although quasi-drug-grade powders have, as a quality standard, a relatively high purity as high as 98.0% by weight or higher in terms of the purity of ascorbic acid 2-glucoside and retain a satisfactory free-flowing ability as a powder (throughout the specification, "powder(s)" means "particulate composition(s)", unless specified otherwise") just after production, they have the defect that they may solidify due to their dead load or moisture absorbency, when allowed to stand under a relatively high temperature and humid conditions for a relatively long period of time. Considering such defect, conventional quasi-drug-grade powders have been commercialized being packed in polyethylene bags by 10 kg aliquots thereof and placed, along with desiccants, in steel cans with covers. Even with the form of such product form, quasi-drug-grade powders, however, still have the problem that they may occasionally solidify and lose their usefulness as powders, when stored for a relatively long period of time. Solidification of particulate compositions, which contain anhydrous crystalline ascorbic acid 2-glucoside to be used as a material for cosmetics, quasi-drugs, or food products, may usually cause troublesome event in the steps of, for example, transporting, sieving, or mixing materials, when a production plant is designed on the premises that materials with satisfactory free-flowing ability will be used.

PRIOR ART LITERATURE i) Patent Literature

[Patent Literature 1] Japanese Patent Kokai No. 139288/91
[Patent Literature 2] Japanese Patent Kokai No. 135992/91
[Patent Literature 3] Japanese Patent Kokai No. 183492/91
[Patent Literature 4] Japanese Patent Kokai No. 117290/93
[Patent Literature 5] Japanese Patent Kokai No. 208991/93
[Patent Literature 6] Japanese Patent Kokai No. 2002-088095
[Patent Literature 7] Japanese Patent Kokai No. 2004-065098
[Patent Literature 8] International Patent Publication No. WO 02010361
[Patent Literature 9] International Patent Publication No. WO 01090338
[Patent Literature 10] International Patent Publication No. WO 05087182
[Patent Literature 11] Japanese Patent Kokai No. 046112/92
[Patent Literature 12] Japanese Patent Kokai No. 182412/92
[Patent Literature 13] Japanese Patent Kokai No. 182413/92
[Patent Literature 14] Japanese Patent Kokai No. 182419/92
[Patent Literature 15] Japanese Patent Kokai No. 182415/92
[Patent Literature 16] Japanese Patent Kokai No. 182414/92
[Patent Literature 17] Japanese Patent Kokai No. 333260/96
[Patent Literature 18] Japanese Patent Kokai No. 2005-239653
[Patent Literature 19] International Patent Publication No. WO 06033412
[Patent Literature 20] Japanese Patent Kokai No. 2002-326924
[Patent Literature 21] Japanese Patent Kokai No. 2003-171290
[Patent Literature 22] Japanese Patent Kokai No. 2004-217597
[Patent Literature 23] International Patent Publication No. WO 05034938
[Patent Literature 24] Japanese Patent Kokai No. 2006-225327
[Patent Literature 25] International Patent Publication No. WO 06137129
[Patent Literature 26] International Patent Publication No. WO 06022174
[Patent Literature 27] Japanese Patent Kokai No. 2007-063177
[Patent Literature 28] International Patent Publication No. WO 06132310
[Patent Literature 29] International Patent Publication No. WO 07086327 ii) Non-Patent Literature

[Non-Patent Literature 1] *Carbohydrate Research*, Takahiko MANDAI et al., Vol. 232, pp. 197-205, 1992

[Non-Patent Literature 2] *International Journal of Pharmaceutics*, Yutaka INOUE et al., Vol. 331, pp. 38-45, 2007

SUMMARY OF THE INVENTION

The present invention, which was made to solve the above defect, aims to provide a particulate composition containing anhydrous crystalline ascorbic acid 2-glucoside that is more significantly, hardly solidifiable than conventional particulate compositions containing anhydrous crystalline ascorbic acid 2-glucoside in a grade for use in quasi-drugs; and to provide a process for producing the same and uses thereof.

In order to overcome the above objects, the present inventors continued studying on the solidification of a particulate composition containing anhydrous crystalline ascorbic acid 2-glucoside, and found that "ASCORBIC ACID 2-GLUCOSIDE 999", a product name of a particulate composition containing anhydrous crystalline ascorbic acid 2-glucoside for use as a standard reagent for analysis, code No. AG124, commercialized by Hayashibara Biochemical Laboratories Inc., Okayama, Japan (abbreviated as "reagent grade powder", hereinafter), does not solidify even under the conditions, where a quasi-drug-grade powder does solidify, and retains properties as a powder. Like a quasi-drug-grade powder, the above reagent grade powder is the one produced by purifying a solution containing ascorbic acid 2-glucoside obtained through a step of allowing CGTase to act on a solution containing L-ascorbic acid and amylaceous substance, concentrating the purified solution, and crystallizing ascorbic acid 2-glucoside to obtain anhydrous crystalline ascorbic acid 2-glucoside. The above reagent grade powder, however, differs from the quasi-drug-grade powder in that, in addition to the ordinary production steps, it requires a recrystallization step of dissolving once obtained crystals and then crystallizing again the same and a washing step of repeatedly washing the recrystallized crystals with refined water, etc., to increase the purity of ascorbic acid 2-glucoside to a level of 99.9% by weight or higher. Thus, even the quasi-drug-grade powder, it can possibly be made into a hardly solidifiable particulate composition containing anhydrous crystalline ascorbic acid 2-glucoside when the purity can be increased to 99.9% by weight or higher.

To increase the purity of anhydrous crystalline ascorbic acid 2-glucoside to a higher purity level as high as at least 99.9% by weight, however, as mentioned above, optional steps of a recrystallization step and a washing step with refined water or the like will be required, in addition to the ordinal production steps, resulting in unfavorably increasing the time and labor required for its production, causing loss of ascorbic acid 2-glucoside in the recrystallization and washing steps, lowering of production yield, and increasing the production cost by a large margin. Therefore, it is not a realistic selection to simply increase the purity of ascorbic acid 2-glucoside to a level of 99.9% by weight or higher in order to obtain a hardly solidifiable particulate composition containing anhydrous crystalline ascorbic acid 2-glucoside than the quasi-drug-grade powder.

The present inventors continued studying on the solidification of a particulate composition containing anhydrous crystalline ascorbic acid 2-glucoside and repeatedly researched in such a manner of trial and error, and they found, compared to conventional quasi-drug-grade powders, a significantly, hardly solidifiable particulate composition containing anhydrous crystalline ascorbic acid 2-glucoside is of which has either an increased degree of crystallinity of 90% or higher for anhydrous crystalline ascorbic acid 2-glucoside, or a decreased dynamic vapor sorption level of the particulate composition of 0.01% by weight or lower, even though the particulate composition has the same level of purity of ascorbic acid 2-glucoside as those of conventional quasi-drug-grade powders or has a purity lesser than those in a reagent grade powder.

The present inventors further continued studying on a process for producing a particulate composition, containing anhydrous crystalline ascorbic acid 2-glucoside with the above-identified degree of crystallinity and having the above-identified dynamic vapor sorption level, on an industrial scale, finding that a particulate composition containing anhydrous crystalline ascorbic acid 2-glucoside prepared by the following steps can be relatively easily made from a powder, containing anhydrous crystalline ascorbic acid 2-glucoside crystallized from the following solution, into a particulate composition with a degree of crystallinity of 90% or higher for anhydrous crystalline ascorbic acid 2-glucoside, and a dynamic vapor sorption level of the particulate composition of 0.01% by weight or lower: Allowing CGTase and glucoamylase in this order to act on a solution containing L-ascorbic acid and amylaceous substance to form ascorbic acid 2-glucoside in a high production yield of 35% by weight or higher, purifying the resulting solution to increase the content of ascorbic acid 2-glucoside up to over 86% by weight, on a dry solid basis (d.s.b.).

The present inventors found that a particulate composition, having a degree of crystallinity of 90% or higher for anhydrous crystalline ascorbic acid 2-glucoside or having a dynamic vapor sorption level of 0.01% by weight or lower, is significantly, hardly solidifiable compared to conventional quasi-drug-grade powders; it is readily handleable as a material for food products, cosmetics, quasi-drugs, and pharmaceuticals; and it has an outstanding significance and value. Thus, they accomplished this invention.

BRIEF DESCRIPTION OF THE ACCOMPANYING DRAWINGS

EXPLANATION OF SYMBOLS

Figure 5:
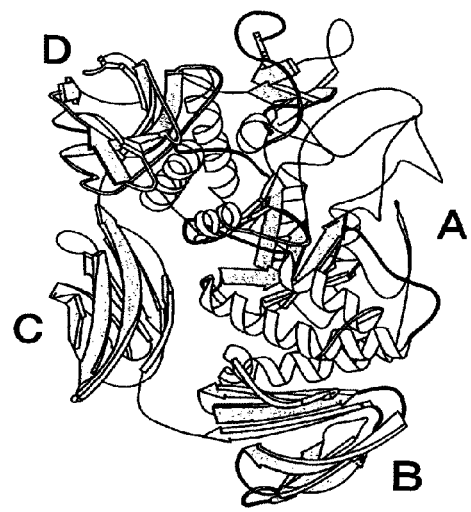
FIG. 5 is a schematic diagram of higher-order structure of CGTase derived from a microorganism of the genus *Geobacillus*.
Figure 6:
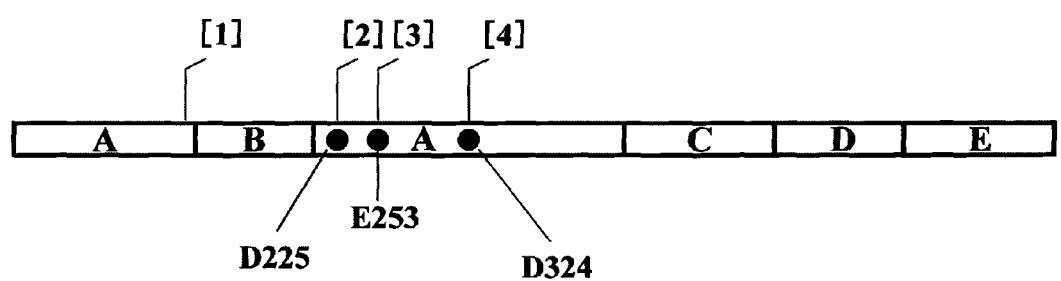
FIG. 6 is a schematic diagram of catalytic residues and conserved regions of CGTase derived from a microorganism of the genus *Geobacillus*.

In FIGS. 5 and 6, the symbols "A" to "D" mean Domain A of CGTase, Domain B of CGTase, Domain C of CGTase, and Domain D of CGTase, respectively.

In FIG. 5, "helix" means an α-helix structure; "plate-like arrow", β-sheet structure; and "fine thread", loop structure.

In FIG. 6, the symbols [1] to [4] mean conserved regions 1 to 4, commonly present in α-amylase family, respectively; the symbol "●", a catalytic residue; "D225", $225^{th}$ aspartic acid residue $253^{rd}$ as one of the catalytic residues of CGTase; "D253", $253^{rd}$ glutamic acid residue as one of the catalytic residues of CGTase; and "D324", $324^{th}$ aspartic acid residue as one of the catalytic residues of CGTase.

Figure 7:
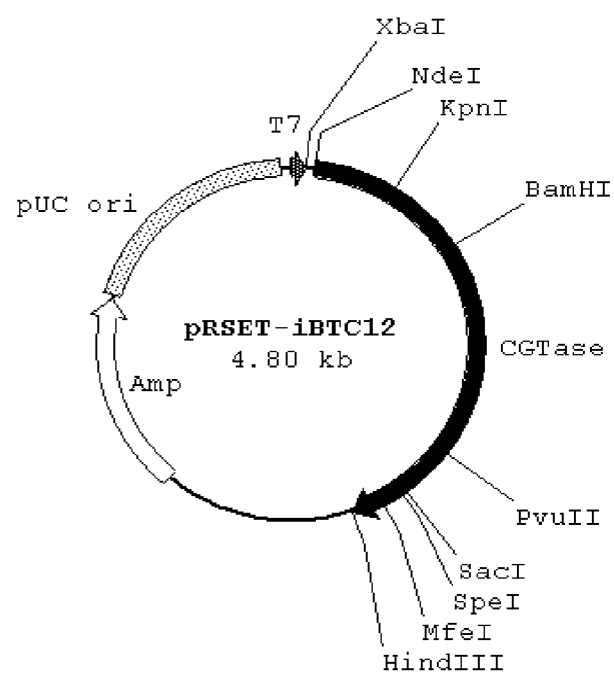
FIG. 7 is a figure of the structure and the restriction enzyme recognition site of a recombinant DNA "pRSET-iBTC12", containing CGTase gene derived from a microorganism of the genus *Geobacillus*, used in the present invention.

In FIG. 7, the symbol "pUC ori" means replication origin of plasmid pUC; "T7", T7 promoter; "white arrow (Amp)", ampicillin resistant gene; and "black arrow", CGTase gene.

DETAILED DESCRIPTION OF THE INVENTION

The present invention solves the above objects by providing a particulate composition, which contains ascorbic acid 2-glucoside in an amount of over 98.0% by weight but less than 99.9% by weight, d.s.b., and has a degree of crystallinity of 90% or higher for anhydrous crystalline ascorbic acid 2-glucoside, when calculated based on a profile of powder X-ray diffraction analysis of the particulate composition.

The present invention solves the above objects by providing a particulate composition containing ascorbic acid 2-glucoside in an amount of over 98.0% by weight but less than 99.9% by weight, d.s.b., and a dynamic vapor sorption level of the particulate composition of 0.01% by weight or lower, when kept at 25° C. under a relative humidity of 35% for 12 hours after removal of water under nitrogen gas stream.

As a preferred embodiment according to the present invention, the particulate composition containing anhydrous crystalline ascorbic acid 2-glucoside of the present invention contains particles with a particle size of less than 150 μm in an amount of 70% by weight or more to the whole particulate composition and those with a particle size of at least 53 μm but less than 150 μm in an amount of 40 to 60% by weight to the whole particulate composition. As another preferred embodiment, the particulate composition containing anhydrous crystalline ascorbic acid 2-glucoside of the present invention contains L-ascorbic acid and/or D-glucose and has a reducing power of the total particulate composition of less than one percent by weight. In a more preferred embodiment, the particulate composition containing anhydrous crystalline ascorbic acid 2-glucoside of the present invention contains L-ascorbic acid in an amount of 0.1% by weight or lower, d.s.b.

The particulate composition containing anhydrous crystalline ascorbic acid 2-glucoside of the present invention as mentioned above is typically a particulate composition produced from a solution containing ascorbic acid 2-glucoside obtained through a step of allowing CGTase to act on a solution containing L-ascorbic acid and amylaceous substance.

The present invention solves the above objects by providing a process for producing a particulate composition containing anhydrous crystalline ascorbic acid 2-glucoside, characterized in that it contains the steps of allowing CGTase and glucoamylase in this order to act on a solution containing L-ascorbic acid and amylaceous substance to obtain a solution containing ascorbic acid 2-glucoside in a production yield of 35% by weight or higher of ascorbic acid 2-glucoside; purifying the resulting solution to increase the content of ascorbic acid 2-glucoside to a level of over 86% by weight, d.s.b.; crystallizing anhydrous crystalline ascorbic acid 2-glucoside in the purified solution; collecting the crystallized anhydrous crystalline ascorbic acid 2-glucoside; and ageing and drying the collected crystals; and optionally pulverizing the resulting crystals.

Examples of the CGTase used in the process of the present invention include any of natural CGTase enzymes and those which are prepared by recombinant DNA technology independently of their origins and sources, as long as they form ascorbic acid 2-glucoside in a production yield of 35% by weight or higher, when CGTase and glucoamylase are allowed in this order to act on a solution containing L-ascorbic acid and amylaceous substance. However, considering the production yield of ascorbic acid 2-glucoside, preferred are the later described CGTases derived from *Geobacillus stearothermophilus* Tc-62 strain and *Geobacillus stearothermophilus* Tc-27 strain, and mutant CGTases obtained by mutating the CGTase derived from *Geobacillus stearothermophilus* Tc-91 strain by recombinant DNA technology. Among which, the CGTase from *Geobacillus stearothermophilus* Tc-62 strain is most preferably used because of its relatively high production yield of ascorbic acid 2-glucoside.

The glucoamylase used in the present invention should not specifically be restricted and any of naturally-occurring and recombinant enzymes can be used independently of their origins and sources, as long as they form ascorbic acid 2-glucoside in a production yield of 35% by weight or higher, when CGTase and glucoamylase are allowed in this order to act on a solution containing L-ascorbic acid and amylaceous substance.

Varying depending on the type of amylaceous substance used as a material, when CGTase is allowed to act on a solution containing L-ascorbic acid and amylaceous substance, the production yield of ascorbic acid 2-glucoside can be increased by allowing to act on the solution a starch debranching enzyme such as isoamylase and pullulanase along with CGTase.

In a preferred embodiment of the process according to the present invention, the step for purifying the above solution containing ascorbic acid 2-glucoside to increase the content of ascorbic acid 2-glucoside to over 86% by weight, d.s.b., is effected by allowing an enzymatic reaction solution after filtration and desalting to contact with an anion-exchange resin to adsorb thereupon ascorbic acid 2-glucoside and L-ascorbic acid, removing saccharides such as D-glucose with refined water, feeding as an eluent an aqueous solution with a concentration of less than 0.5 N of hydrochloric acid or salt(s) to elute ascorbic acid 2-glucoside and L-ascorbic acid, concentrating the resulting eluate, feeding the concentrated eluate to column chromatography using a cation-exchange resin or a porous synthetic resin, and feeding an eluent to effect elution. Particularly, as column chromatography with cation-exchange resin, those of simulated-moving-bed system using a strong-acid cation-exchange resin as a packing material are preferable because a desired fraction with an ascorbic acid 2-glucoside content of over 86% by weight is preferably obtained therewith at a satisfactory efficiency and production yield.

The present invention solves the above objects by providing a powderous material for food products, cosmetics, quasi-drugs, and pharmaceuticals, which consists of the particulate composition containing anhydrous crystalline ascorbic acid 2-glucoside of the present invention.

Examples of the materials for food products advantageously usable in the present invention include vitamin-C-enriching agents, collagen-production enhancers, skin-whitening agents, taste-improving agents, quality-improving agents, browning-preventing agents, acidulants, fillers, body-imparting agents, and antioxidants. Examples of the materials for cosmetics advantageously usable in the present invention include skin-whitening agents, cell-activating agents, collagen-production enhancers, vitamin-C-enriching agents, taste-improving agents, quality-improving agents, browning-preventing agents, acidulants, fillers, body-imparting agents, stabilizers, and antioxidants. Examples of the materials for quasi-drugs advantageously usable in the present invention include skin-whitening agents, cell-activating agents, collagen-production enhancers, vitamin-C-enriching agents, taste-improving agents, quality-improving agents, browning-preventing agents, acidulants, fillers, body-imparting agents, stabilizers, and antioxidants. Further, examples of the materials for pharmaceuticals advantageously usable in the present invention include skin-whitening agents, cell-activating agents, collagen-production enhancers, agents for preserving organs, radical-disorder-inhibitory agents, vitamin-C-enriching agents, browning-preventing agents, fillers, adjuvants, stabilizers, and antioxidants.

The following are detailed explanations of the present invention:

1. Definition of Terms

Throughout the specification, the following terms mean as follows:

<Degree of Crystallinity>

The term "a degree of crystallinity for anhydrous crystalline ascorbic acid 2-glucoside" as referred to as in the specification means a value defined by the following Formula [1].

$$\text{Degree of crystallinity} (\%) = \frac{Hs - H_0}{H_{100} - H_0} \times 100 \qquad \text{Formula [1]}$$

$H_{100}$: An analytical value for a degree of crystallinity, determined based on the powder X-ray diffraction profile for a powdery standard sample containing anhydrous crystalline ascorbic acid 2-glucoside, where the powdery standard sample consists substantially of anhydrous crystalline ascorbic acid 2-glucoside.

$H_0$: An analytical value for a degree of crystallinity, determined based on the powder X-ray diffraction profile for a powdery standard sample containing ascorbic acid 2-glucoside, where the powdery standard sample consists substantially of amorphous form of ascorbic acid 2-glucoside.

Hs: An analytical value for a degree of crystallinity, determined based on the powder X-ray diffraction profile for, as a test sample, a powder containing ascorbic acid 2-glucoside.

In Formula [1], the powder X-ray diffraction profiles for the basis of determining analytical values $H_{100}$, $H_0$ and Hs can be usually determined by a powder X-ray diffraction analyzer equipped with a reflective or transmissive optical system. The powder X-ray diffraction profiles contain data for diffraction angles and diffraction strengths of anhydrous crystalline ascorbic acid 2-glucoside contained in a test or standard sample. Examples of methods for determining the analytical data for the degrees of crystallinity of such samples include Harmans' method, Vonk' s method, etc. Among which Harmans' method is preferable because of its easiness and accuracy. Since these analytical methods have now been provided as computer softwares, any powder X-ray diffraction analyzers, equipped with an analytical apparatus installed with any of the above computer softwares, can be suitably used.

As "a powdery standard sample containing anhydrous crystalline ascorbic acid 2-glucoside, where the powdery standard sample consists substantially of anhydrous crystalline ascorbic acid 2-glucoside", for determining analytical value $H_{100}$, there must be used an anhydrous crystalline ascorbic acid 2-glucoside in the form of a particulate composition or single crystal, which has a purity of 99.9% by weight or higher (throughout the specification, "% by weight" is abbreviated as "%", unless specified otherwise but the "%" affixed to the degree of crystallinity should not be limited thereunto), exhibits characteristic diffraction peaks inherent to anhydrous crystalline ascorbic acid 2-glucoside, and consists substantially of anhydrous crystalline ascorbic acid 2-glucoside. Examples of those in the form of a particulate composition or single crystal include those in the form of a particulate composition of any of the above-identified reagent grade powder, particulate compositions containing anhydrous crystalline ascorbic acid 2-glucoside obtained by recrystallizing the reagent grade powder, or anhydrous crystalline ascorbic acid 2-glucoside in the form of a single crystal. For reference, when analyzed with a computer software for Harmans' method, a powder X-ray diffraction profile of the above-identified powdery standard sample of particulate composition containing anhydrous crystalline ascorbic acid 2-glucoside, which consists substantially of anhydrous crystalline ascorbic acid 2-glucoside, gives an analytical value $H_{100}$, usually, ranging from about 70.2% to about 70.5%.

As "a powdery standard sample containing ascorbic acid 2-glucoside, where the powdery standard sample consists substantially of amorphous form of ascorbic acid 2-glucoside" for determining analytical value $H_0$, it must be used an ascorbic acid 2-glucoside in the form of a particulate composition, which has a purity of 99.1% or higher, exhibits a powder X-ray diffraction pattern of only halo inherent to its amorphous form, and does not substantially exhibit any diffraction peak of anhydrous crystalline ascorbic acid 2-glucoside. Examples of such a particulate composition include those which are obtained by dissolving the above-identified powdery standard sample for determining the analytical value $H_{100}$ in an appropriate amount of refined water, concentrating the solution, freeze-drying the concentrate, and drying the resultant in vacuo up to give a moisture content of 2.0% or lower, when determined on Karl Fischer method. With these treatment, it is known by experience that a particulate composition consisting substantially of an amorphous form is obtained. For reference, when analyzed with a computer software for Harmans' method, a powder X-ray diffraction profile of the above-identified powdery standard sample of particulate composition containing ascorbic acid 2-glucoside, which consists substantially of amorphous form of ascorbic acid 2-glucoside, gives an analytical value $H_0$, usually, ranging from about 7.3% to about 7.6%.

As a standard sample for determining analytical value $H_0$, it goes without saying that an ascorbic acid 2-glucoside with a higher purity is preferable, however, the purity of ascorbic acid 2-glucoside of a standard sample used for determining the analytical value $H_0$, prepared from the standard sample used for determining analytical value $H_{100}$ as mentioned above, is limited up to 99.1%, even thought the purity of the standard sample used for determining analytical value $H_{100}$ is distinctly as high as 99.9% or higher, as shown in the later described Experiment 1-1. Thus, the purity of "a powdery standard sample containing ascorbic acid 2-glucoside, where the powdery standard sample consists substantially of amorphous form of ascorbic acid 2-glucoside" is set to 99.1% or higher as mentioned above.

<Dynamic Vapor Sorption Level>

The term "dynamic vapor sorption level" as referred to as in the specification means a value calculated by the following Formula [2] based on two weight values determined on a moisture sorption/desorption analyzer in such a manner of removing free water from a sample by allowing it to stand at 25° C. and a relative humidity of 0% under nitrogen gas stream for 12 hours, and weighing the resulting sample; and by allowing the sample to stand at 25° C. and a relative humidity of 35% under nitrogen gas stream for 12 hours, and immediately weighing the resulting sample again:

$$\text{Dynamic vapor sorption level (\%)} = \frac{W_{35\%} - W_{0\%}}{W_{0\%}} \times 100 \quad \text{Formula [2]}$$

$W_{0\%}$ Weight of a test sample measured immediately after standing at 25° C. and a relative humidity of 0% under nitrogen gas stream for 12 hours.

$W_{35\%}$ Weight of a test sample measured immediately after the test sample, which had been measured for $W_0$%, was allowed to stand at 25° C. and a relative humidity of 35% under nitrogen gas stream for 12 hours.

<Reducing Power>

The term "reducing power of the whole particulate composition" as referred to as in the specification means a percent (%) of the reducing saccharide content to the total sugar content in a test sample, calculated by the following Formula [3] based on the reducing sugar content and the total sugar content in term of D-glucose determined on Somogyi-Nelson's method and anthrone-sulfuric acid method widely used in the art, where D-glucose is used as a standard substance.

$$\text{Reducing power (\%)} = \frac{\text{Reducing sugar content}}{\text{Total sugar content}} \times 100 \quad \text{Formula [3]}$$

<Particle Size Distribution>

In the specification, the particle size distribution of a particulate composition is determined as follows: Metal sieves with opening sizes of 425, 300, 212, 150, 106, 75 and 53 µm, produced by Kabushiki Gaisha Iida Seisaku-sho, which are compliant with Japanese Industrial Standards (JIS Z 8801-1), are accurately weighed, stacked in the above-identified order, and mounted on "R-1", a ro-tap sieving shaker, produced by Kabushiki Gaisha Tanaka Kagaku Kikai Seisaku-sho. A prescribed amount of weighed sample is placed on the uppermost sieve (having an opening size of 425 µm) among the stacked sieves, followed by shaking the sieves for 15 min while keeping the stacked conditions. Thereafter, each of the stacked sieves was accurately weighed, and the weight of the sample collected on each of the sieves was determined by subtracting the weight of each of the sieves before loading the sample from the weight of the corresponding sieve after shaking. Particle size distribution is expressed by calculating the weight percentage (%) of the weight of the particulate composition collected on each of the sieves to that of the loaded sample.

<Production Yield of Ascorbic Acid 2-Glucoside>

The term "production yield of ascorbic acid 2-glucoside" as referred to as in the specification means a content (%) of ascorbic acid 2-glucoside, d.s.b., in an enzymatic reaction solution obtained by allowing an enzyme such as CGTase to act on a solution containing L-ascorbic acid and amylaceous substance.

<Content of Ascorbic Acid 2-Glucoside, d.s.b.>

The term content of ascorbic acid 2-glucoside, d.s.b., means a percentage (%) by weight of ascorbic acid 2-glucoside to the total weight of a sample containing the same when calculated excluding water. For example, the meaning of the content of ascorbic acid 2-glucoside, d.s.b., in a solution is a percentage (%) by weight of ascorbic acid 2-glucoside to the total solid contents, excluding water contained in the solution. While the meaning of the content of ascorbic acid 2-glucoside, d.s.b., in a particulate composition is a percentage (%) by weight of the weight of ascorbic acid 2-glucoside to the total weight of the particulate composition, when calculated by regarding the total weight of the particulate composition as that excluding water contained in the particulate composition.

<CGTase Activity>

The term "CGTase activity" as referred to as in the specification is defined as follows: To five milliliters of an aqueous substrate solution containing 0.3% (w/v) of a soluble starch, 20 mM acetate buffer (pH 5.5), and 1 mM calcium chloride, is added 0.2 ml of an enzyme solution diluted appropriately, and the resulting solution is kept at 40° C., and sampled at 0 min and 10 min after initiating the enzymatic reaction in respective amounts of 0.5 ml, followed by immediately adding 15 ml of 0.02 N sulfuric acid solution to each sample to suspend the enzymatic reaction. Each of the resulting solutions is admixed with 0.2 ml of 0.2 N iodine solution to develop colors, and, after 10 min, the colored solutions are respectively measured for absorbance at a wavelength of 660 nm by a spectrophotometer, followed by calculating CGTase activity using the following Formula [4] as an activity for starch hydrolysis. One unit activity of CGTase is defined as the enzyme amount that completely diminishes the iodine color of a solution containing 15 mg of starch.

$$\text{Activity (unit/ml)} = \frac{Aa - Ab}{Aa} \times \frac{1}{0.2} \times (\text{dilution rate}) \quad \text{Formula [4]}$$

Note: "Aa" means the absorbance at a wavelength of 660 nm of a reaction solution at 0 min after initiating the enzymatic reaction.

"Ab" means the absorbance at a wavelength of 660 nm of a reaction solution at 10 min after initiating the enzymatic reaction.

<Isoamylase Activity>

The term "isoamylase activity" as referred to as in the specification is defined as follows:

To three milliliters of an aqueous substrate solution containing 0.83% (w/v) of Lintner soluble waxy corn starch and 0.1 M acetate buffer (pH 3.5) is added 0.5 ml of an appropriately diluted enzyme solution, and the resulting solution is kept at 40° C. and sampled at 0.5 min and 30.5 min after the initiation of enzymatic reaction in respective amounts of 0.5 ml, followed by immediately adding 15 ml of 0.02 N sulfuric acid solution to each sample to suspend the enzymatic reaction. Each of the resulting solutions is admixed with 0.5 ml of 0.01 N iodine solution to develop colors at 25° C. for 15 min, and then the colored solutions are respectively measured for absorbance at a wavelength of 610 nm by an absorptiometer, followed by calculating isoamylase activity using the following Formula [5] as an activity for starch hydrolysis. One unit activity of isoamylase is defined as an enzyme amount that increases the absorbance by 0.004 at a wavelength of 610 nm under the above measurement conditions.

$$\text{Activity (unit/ml)} = \frac{Aa - Ab}{0.004} \times (\text{dilution rate}) \quad \text{Formula [5]}$$

Note: "Aa" means the absorbance of a reaction solution at a wavelength of 610 nm.

"Ab" means the absorbance of a control solution at a wavelength of 610 nm.

2. Particulate Composition Containing Anhydrous Crystalline Ascorbic acid 2-Glucoside of the Present Invention <Degree of Crystallinity and Dynamic Vapor Sorption Level>

As described above, the particulate composition containing anhydrous crystalline ascorbic acid 2-glucoside of the present invention contains over 98.0% but less than 99.9%, d.s.b., of ascorbic acid 2-glucoside; and has a degree of crystallinity of 90% or higher for anhydrous crystalline ascorbic acid 2-glucoside, when calculated based on a profile of powder X-ray diffraction analysis; or has a dynamic vapor sorption level of 0.01% or lower. As explained by the following Experiments, the particulate composition containing anhydrous crystalline ascorbic acid 2-glucoside of the present invention, having the above degree of crystallinity or the dynamic vapor sorption level, is significantly, hardly solidifiable compared to quasi-drug-grade powders, even though it has substantially the same level of purity of ascorbic acid 2-glucoside as those of quasi-drug-grade powders or has a lesser purity of ascorbic acid 2-glucoside than that of a reagent grade powder.

Further, as shown in the following Experiments, among the particulate compositions containing over 98.0% but less than 99.9%, d.s.b., of ascorbic acid 2-glucoside, those with a degree of crystallinity within the above range have a dynamic vapor sorption level of 0.01% or lower, while those with a dynamic vapor sorption level within the above range have a degree of crystallinity of 90% or higher for anhydrous crystalline ascorbic acid 2-glucoside. Thus, the particulate composition containing anhydrous crystalline ascorbic acid 2-glucoside of the present invention can be defined by either of the degree of crystallinity for anhydrous crystalline ascorbic acid 2-glucoside or the dynamic vapor sorption level of the particulate composition, and, if necessary it can be defined by both.

The meaning of dynamic vapor sorption is a phenomenon where the vapor level contained in a sample changes as the humidity around the sample is changed at a constant temperature. Although, unlike degree of crystallinity, dynamic vapor sorption level as a representative index for susceptibility of vapor sorption is not an index that depends directly on the crystalline structure of a powder as a sample, it can be speculated that moisture absorbing phenomenon relates to the solidification of the particulate composition and may significantly change, depending on the saccharide composition, as well as the purity of ascorbic acid 2-glucoside and the particle size of the particulate composition. Thus, it is considered that dynamic vapor sorption level would be a powerful index for evaluating the solidification of particulate composition by moisture absorption.

As found in the following Experiments, a particulate composition containing anhydrous crystalline ascorbic acid 2-glucoside with a dynamic vapor sorption level of over 0.05% relatively easily solidifies under the tested Experimental conditions, while those with a dynamic vapor sorption level of 0.01% or lower do not substantially solidify under the same conditions. The fact indicates that the dynamic vapor sorption level along with the degree of crystallinity are powerful indexes in realizing a substantially, hardly solidifiable particulate composition containing anhydrous crystalline ascorbic acid 2-glucoside.

The standard sample used for determining the analytical value $H_0$ in obtaining the degree of crystallinity, i.e., "a powdery standard sample containing ascorbic acid 2-glucoside, which consists substantially of amorphous form of ascorbic acid 2-glucoside" exhibited a dynamic vapor sorption level of 1.7% as shown in the later described Experiment 3; while the standard sample used for determining the analytical value $H_{100}$ in obtaining the degree of crystallinity, i.e., "a powdery standard sample containing anhydrous crystalline ascorbic acid 2-glucoside, which consists substantially of anhydrous crystalline form of ascorbic acid 2-glucoside" exhibited a dynamic vapor sorption level of lower than detection limit and did not substantially show any dynamic vapor sorption, as shown similarly in Experiment 3.

<Particle Size Distribution>

In a preferred embodiment of the particulate composition containing anhydrous crystalline ascorbic acid 2-glucoside of the present invention, it contains particles with a particle size of less than 150 μm in an amount of 70% or more of the whole particulate composition, and contains those with a particle size of 53 μm or more but less than 150 μm in an amount of 40 to 60% of the whole particulate composition. Since the particulate composition containing anhydrous crystalline ascorbic acid 2-glucoside of the present invention can be, for example, easily controlled within the above-identified particle size distribution required in materials for food products, it has the merit that it can be used as a material for food products, cosmetics, quasi-drugs, or pharmaceuticals similarly as conventional ones without altering any conventional production steps or material regulations.

<Reaction Impurities and Reducing Power>

In a preferred embodiment of the particulate composition containing anhydrous crystalline ascorbic acid 2-glucoside of the present invention, it contains L-ascorbic acid and/or D-glucose and has a reducing power of the whole particulate composition being less than one percent. As well known, L-ascorbic acid and D-glucose have direct reducibility and induce brown coloration when heated in the coexistence of a compound having amino group intramolecularly, such as amino acids and proteins, and therefore they should not preferably be present in a particulate composition containing anhydrous crystalline ascorbic acid 2-glucoside as a product. However, for example, in producing a particulate composition, containing anhydrous crystalline ascorbic acid 2-glucoside, obtained through a step of allowing an enzyme such as CGTase to act on a solution containing L-ascorbic acid and amylaceous substance, reaction impurities such as intact L-ascorbic acid and D-glucose derived from the material amylaceous substance will inevitably coexist in thus produced particulate composition at any rate. For example, in conventional quasi-drug-grade powders, the amounts of L-ascorbic acid and D-glucose contained therein could reach about one percent, d.s.b., in total, and this may induce unpredictable browning reaction when used as materials for food products, etc.

Thus, in the present invention, while permitting unavoidable incorporation of L-ascorbic acid and/or D-glucose, the reducing power of the whole particulate composition of the particulate composition containing anhydrous crystalline ascorbic acid 2-glucoside is controlled to less than one percent. As shown in the later described Experiments, in producing the particulate composition containing anhydrous crystalline ascorbic acid 2-glucoside of the present invention by the process according to the present invention, the reducing power of the whole particulate composition can be easily adjusted to less than one percent. As long as the reducing power of the whole particulate composition is less than one percent, particulate compositions containing anhydrous crystalline ascorbic acid 2-glucoside, which even contain L-ascorbic acid and/or D-glucose, do not substantially induce brown coloration even when heated in the presence of a compound with amino group intramolecularly such as amino acids and proteins. Accordingly, any particulate compositions containing anhydrous crystalline ascorbic acid 2-glucoside, which contain L-ascorbic acid and/or D-glucose and have a reducing power of each whole particulate composition being less than one percent, have the merit that they can be incorporated into food products, cosmetics, quasi-drugs, and pharmaceuticals in general without fear of causing coloration and color change. In this connection, when the reducing power of the whole particulate composition is less than one percent, the total content of L-ascorbic acid and D-glucose is 0.2% or lower, d.s.b., to the particulate composition.

In a more preferred embodiment, the particulate composition containing anhydrous crystalline ascorbic acid 2-glucoside of the present invention has an L-ascorbic acid content of 0.1% or lower, d.s.b. As used in food products or the like as an antioxidant or oxygen scavenger, L-ascorbic acid is high in reactivity with oxygen. Because of this, it is considered that L-ascorbic acid not only induces brown coloration when heated in the presence of compounds having amino groups intramolecularly, but also distinctly relates to the coloration of particulate compositions per se. In fact, as shown in the later described Experiment, according to the finding obtained by the present inventors, quasi-drug-grade powders which contain about 0.2% of L-ascorbic acid occasionally induce a phenomenon that they in themselves become to show pale brown coloration, when stored in the above mentioned form for a relatively long period of time. In contrast, in the case that a particulate composition containing anhydrous crystalline ascorbic acid 2-glucoside has an L-ascorbic acid content of 0.1% or lower, it in itself is free of causing fear of pale brown coloration even when stored in the same product form as the quasi-drug-grade powders. For reference, according to the production process of the present invention, the L-ascorbic acid content in the particulate composition containing anhydrous crystalline ascorbic acid 2-glucoside of the present invention can be relatively easily made 0.1% or lower without increasing production cost through the purification step of, successively conducting column chromatography using anion-exchange resin to remove saccharides such as D-glucose, etc., and then column chromatography using cation-exchange or porous resin, particularly, applying simultaneous-moving-bed column chromatography using cation-exchange resin as the column chromatography using cation-exchange resin.

3. Process for Producing the Particulate Composition Containing Anhydrous Crystalline Ascorbic Acid 2-Glucoside of the Present Invention The particulate composition containing anhydrous crystalline ascorbic acid 2-glucoside of the present invention can be the one prepared by any production process and should not be restricted to specific one produced by a particular production process, as long as it is a particulate composition containing anhydrous crystalline ascorbic acid 2-glucoside, which contains ascorbic acid 2-glucoside in an amount of over 98.0% but less than 99.9%, d.s.b., and has either a degree of crystallinity of 90% or higher for anhydrous crystalline ascorbic acid 2-glucoside or a dynamic vapor sorption level of 0.01% or lower.

However, according to the following process of the present invention, the particulate composition containing anhydrous crystalline ascorbic acid 2-glucoside of the present invention is relatively easily produced; the process basically contains the following steps (1) to (5):

(1) Allowing CGTase and glucoamylase in this order to act on a solution containing L-ascorbic acid and amylaceous substance to obtain a solution containing ascorbic acid 2-glucoside in a production yield of 35% or higher;
(2) purifying the resulting solution containing ascorbic acid 2-glucoside to increase the content of ascorbic acid 2-glucoside to over 86%, d.s.b.;
(3) subjecting the resulting purified solution with an ascorbic acid 2-glucoside content of over 86%, d.s.b., to crystallize ascorbic acid 2-glucoside to form anhydrous crystalline ascorbic acid 2-glucoside;
(4) collecting the formed anhydrous crystalline ascorbic acid 2-glucoside; and
(5) ageing, drying, and optionally, pulverizing the collected anhydrous crystalline ascorbic acid 2-glucoside.

The above steps are respectively explained below:
<Step (1)>
Step (1) is for forming ascorbic acid 2-glucoside from L-ascorbic acid and amylaceous substance through an enzymatic reaction. The materials and enzymes used and the enzymatic reaction employed are successively explained.
A. Materials and Enzymes Used
<L-Ascorbic Acid>
Examples of the L-ascorbic acid used in the present invention include any of those in the form of a hydroxy acid or a metal salt thereof such as alkaline metal salts and alkaline earth metal salts, and even mixtures thereof can be used without difficulty.
<Amylaceous Substance>
Examples of the amylaceous substance used in the present invention include potato starch, sweet potato starch, tapioca starch, corn starch, wheat starch, etc. Among which, those, which do not substantially have any branched structure intramolecularly but have a uniform glucose polymerization degree, are preferable; cyclomaltodextrins, cycloamyloses, synthesized amyloses, etc., are particularly preferable because they all have a glucose polymerization degree of 6 to 100 and have a straight-chain structure or a straight-chain cyclic structure. When liquefied starches in general and partial starch hydrolysates are used as the amylaceous substance, they are preferably controlled their glucose polymerization degrees by hydrolyzing the branched sites of such starches by using CGTase in combination with, for example, a starch debranching enzyme(s) such as isoamylase (EC 3.2.1.68) and pullulanase (EC 3.3.1.41). Isoamylase is particularly preferable as such starch debranching enzymes because it is readily handleable depending on its enzymatic activity, substrate specificity, etc.
<CGTase>
Examples of the CGTase (EC 2.4.1.19) used in the present invention include any of those of natural origins or those which are obtained by recombinant technology without particularly restricting to their origins and sources, as long as they form ascorbic acid 2-glucoside in a production yield as high as about 35% or higher, when allowed successively along with glucoamylase in this order to act on a solution containing L-ascorbic acid and amylaceous substance. Examples of such enzymes of natural origins include CGTases derived from *Geobacillus stearothermophilus* Tc-62 strain and *Geobacillus stearothermophilus* Tc-27 strain are preferable because of their relatively high production yield of ascorbic acid 2-glucoside; among which, the former CGTase derived from *Geobacillus stearothermophilus* Tc-62 strain is most preferable in terms of the production yield of ascorbic acid 2-glucoside.

Examples of CGTase obtained through recombinant DNA technology include, for example, the one having an amino acid sequence, wherein the $228^{th}$ lysine residue in the amino acid sequence of CGTase produced by *Geobacillus stearothermophilus* Tc-91 strain, i.e., the amino acid sequence SEQ ID NO: 1, has been replaced with glutamic acid residue. To obtain such mutant CGTase, as well known, a gene encoding the amino acid sequence, wherein the $228^{th}$ lysine residue in the amino acid sequence SEQ ID NO: 1 has been replaced with glutamic acid residue, is introduced into an appropriate host such as *E. coli, Bacillus subtilis*, etc., to transform the host, followed by expressing the gene in the transformant.

The above-identified *Geobacillus stearothermophilus* Tc-27, Tc-62 and Tc-91 strains are the microorganisms disclosed in Japanese Patent Kokai No. 63189/75 (Japanese Patent Publication No. 27791/78) applied for by the same applicant as the present invention, and they have been deposited in National Institute of Bioscience and Human-Technology Agency of Industrial Science and Technology, Higashi 1-1-1, Chuo-6, Tsukuba-shi, Ibaraki, Japan, under the accession numbers of FERM BP-11142, FERM BP-11143, and FERM P-2225 (under transferring procedure to International Deposit under the accession number of FERM ABP-11273), when confirmed on the day of Jul. 14, 2009. Microorganisms which were once classified into a group under the name of those of the species *Bacillus stearothermophilus* have now been all transferred to a group under the name of microorganisms of the species "*Geobacillus stearothermophilus*", however, the name of microorganisms of the genus "*Bacillus*" still has been used as that for calling the microorganisms of an independent genus. Under these circumstances, to avoid confusion, the microorganisms of the species "*Bacillus stearothermophilus*" and "*Geobacillus stearothermophilus*" are described as those of the species "*Geobacillus stearothermophilus*" throughout the specification.
<Glucoamylase>
Any glucoamylases (EC 3.2.1.3) can be used without specific restriction independently of their origins and sources and they include those in the form of a natural enzyme and those obtained by recombinant DNA technology, as long as CGTase and glucoamylase, when allowed in this order to act on a solution containing L-ascorbic acid and amylaceous substance, form ascorbic acid 2-glucoside in a production yield as high as 35% or higher.

Since glucoamylase is usually added to an enzymatic reaction solution after the solution is heated to suspend the saccharide-transferring reaction by CGTase, those which can exert a desired enzymatic activity suitable for actual use at a relatively high temperature, for example, about 40 to about 60° C. so as to save energy and time needed for cooling the enzymatic reaction after heating. In use, when glucoamylase contains α-glucosidase, the resulting ascorbic acid 2-glucoside will be hydrolyzed thereby, and glucoamylase substantially free of α-glucosidase is desirably used. Any glucoamylases can be used independently of their origins and sources as long as they fulfill the above requirements, for example, commercialized a glucoamylase preparation derived from a microorganism of the genus *Rhizopus*, a product name of "GLUCOZYME #20000", an enzyme commercialized by Nagase ChemteX, Corp., Osaka, Japan; and others derived from a microorganism of the genus *Aspergillus*, a product name of "GLUCZYME AF6" commercialized by Amano Enzyme Inc., Aichi, Japan, can be preferably used.

B. Enzymatic Reaction

The following explain the saccharide-transferring reaction to L-ascorbic acid. CGTase is allowed to act on a solution, usually, an aqueous solution containing L-ascorbic acid and amylaceous substance. When CGTase acts on such an aqueous solution, one or more D-glucose residues are transferred to the hydroxyl group at the C-2 position of L-ascorbic acid, resulting in forming ascorbic acid 2-glucoside with one D-glucose residue bound to the hydroxyl group at the above C-2 position, and other α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid, which have at least two D-glucose residues bound to the hydroxyl group at the above C-2 position.

CGTase is usually allowed to act on an aqueous solution, previously prepared to dissolve L-ascorbic acid and amylaceous substance to give a substrate concentration of 1 to 40%, in an amount of 1 to 500 units/g amylaceous substance, followed by an enzymatic reaction at a pH of about 3 to about 10 and a temperature of 30 to 70° C. for at least six hours, preferably, about 12 to about 96 hours. Since L-ascorbic acid is susceptible to oxidation, the solution should preferably be kept under anaerobic or reducing conditions during enzymatic reaction, while shielding light and optionally coexisting, for example, a reducing agent such as thiourea or hydrogen sulfide.

The weight ratio, d.s.b., of the amylaceous substance and L-ascorbic acid in the solution should preferably be 8:2 to 3:7. When the ratio of amylaceous substance exceeds the above range, saccharide-transfer to L-ascorbic acid effectively proceeds; however, the production yield of ascorbic acid 2-glucoside is restricted by the initial concentration of L-ascorbic acid, resulting in a relatively low level. While, when the ratio of L-ascorbic acid exceeds the above range, intact L-ascorbic acid will remain in a considerable amount and this is not preferable on an industrial-scale production. Accordingly, the above-identified ratio is considered the best.

In addition to CGTase, in the case of using isoamylase as a starch-debranching enzyme, such isoamylase should preferably be allowed to act on amylaceous substance in the coexistence with CGTase in a solution containing L-ascorbic acid and amylaceous substance, wherein the amount of isoamylase to be added is usually 200 to 2,500 units/g amylaceous substance and the enzyme is enzymatically reacted at a temperature of 55° C. or lower, varying depending of the optimum temperature and pH of the isoamylase used. When pullulanase is used as a starch-debranching enzyme, it can be used in accordance with the case of isoamylase.

After an enzymatic reaction with CGTase alone or along with a starch-debranching enzyme is completed as a whole, the resulting enzymatic reaction solution is instantly heated to inactivate the CGTase alone or in combination with the starch-debranching enzyme and to suspend the enzymatic reaction, followed by allowing glucoamylase to act on the resulting solution. By the action of glucoamylase, a chain of two or more D-glucose residues bound to the hydroxyl group at the C-2 position of L-ascorbic acid is cleaved to transform α-glycosyl-L-ascorbic acid such as 2-O-α-maltosyl-L-ascorbic acid, 2-O-α-maltotriosyl-L-ascorbic acid, and 2-O-α-maltotetraosyl-L-ascorbic acid into ascorbic acid 2-glucoside in an increased production yield as high as 35% or higher, preferably, 37 to 45% of ascorbic acid 2-glucoside.

In the case of the production yield of ascorbic acid 2-glucoside being 35% or higher, preferably, 37 to 45%, it facilitates to obtain a particulate composition containing anhydrous crystalline ascorbic acid 2-glucoside having a degree of crystallinity of 90% or higher for anhydrous crystalline ascorbic acid 2-glucoside, or a dynamic vapor sorption level of 0.01% or lower of the particulate composition through the following steps (2) to (5). The reason why the upper limit of the preferable production yield is set to 45% is as follows: It is substantially difficult to exceed the upper limit in view of the today's enzyme engineering technological level, while even if the production yield of ascorbic acid 2-glucoside is increased to over 45%, the degree of crystallinity for anhydrous crystalline ascorbic acid 2-glucoside in the resulting particulate composition and the dynamic vapor sorption level thereof would not so improved.

In the case of the production yield of ascorbic acid 2-glucoside is less than 35%, it is difficult to obtain a particulate composition containing anhydrous crystalline ascorbic acid 2-glucoside having a degree of crystallinity of 90% or higher for anhydrous crystalline ascorbic acid 2-glucoside, or a dynamic vapor sorption level of 0.01% or lower of the particulate composition even if prepared through the following steps (2) to (5). Although the reason is uncertain, it can be speculated that the above difficulty would be dependent upon a relative amount of 5-O-α-glucosyl-L-ascorbic acid and 6-O-α-glucosyl-L-ascorbic acid as by-products that are inevitably formed when CGTase is allowed to act on a solution containing L-ascorbic acid and amylaceous substance.

In general, 5-O-α-glucosyl-L-ascorbic acid and 6-O-α-glucosyl-L-ascorbic acid, where D-glucose residue binds to the hydroxyl group at the C-5 or C-6 position of L-ascorbic acid, are recognized as crystallization-inhibitory substances which inhibit the crystallization of ascorbic acid 2-glucoside, and these 5-O-α-glucosyl-L-ascorbic acid and 6-O-α-glucosyl-L-ascorbic acid are inevitably formed as by-products along with ascorbic acid 2-glucoside and the above-mentioned α-glycosyl-L-ascorbic acids. The content of the above by-products is usually as low as about one percent, d.s.b., in total; however, the removal thereof is generally difficult because these saccharide-transferred products are eluted at substantially the same position as that of ascorbic acid 2-glucoside in conventional purification step with a column. However, when ascorbic acid 2-glucoside is formed in a production yield as high as 35% or higher, preferably, 37 to 45% by allowing the aforementioned natural or recombinant CGTase to act on a solution containing L-ascorbic acid and amylaceous substance, the production yield of 5-O-α-glucosyl-L-ascorbic acid and 6-O-α-glucosyl-L-ascorbic acid does not exceed 0.5%, d.s.b., in total. As a result, it can be speculated that the subsequent crystallization of ascorbic acid 2-glucoside in a particulate composition of anhydrous crystalline ascorbic acid 2-glucoside will proceed more smoothly.

Further, it can be also speculated that the following relate to the above theory; when CGTase is used as a saccharide-transferring enzyme, the binding fashion between D-glucose residues in α-glycosyl-L-ascorbic acid such as 2-O-α-maltosyl-L-ascorbic acid, 2-O-α-maltotriosyl-L-ascorbic acid, etc., is the α-1,4 linkage, even when two or more D-glucose residues are transferred to the hydroxyl group at the C-2 position of L-ascorbic acid. Therefore, the binding between the above D-glucose residues is easily cleaved by the subsequent action of glucoamylase to convert the glycosyl-L-ascorbic acid into ascorbic acid 2-glucoside; and, for example, there is no fear of remaining of crystallization-inhibitory substances, such as α-glycosyl-L-ascorbic acid having a branched structure such as the α-1,6 linkage, even after the glucoamylase treatment, like when α-isomaltosyl glucosaccharide-forming enzyme is used, for example.

<Step (2)>

Step (2) is for purifying a solution containing ascorbic acid 2-glucoside obtained in the above Step (1) to increase the content of ascorbic acid 2-glucoside to over 86%, d.s.b.; the solution containing ascorbic acid 2-glucoside obtained in Step (1) is decolored and filtered with an activated charcoal, etc., followed by desalting the resulting filtrate with a cation-exchange resin and applying the desalted solution to column chromatography to purify the solution to give a content of ascorbic acid 2-glucoside over 86%, preferably, 88% or higher, d.s.b. As the column chromatography used for purification, basically, any column chromatographies can be used as long as they increase the ascorbic acid 2-glucoside content in a solution to over 86%, d.s.b., however, preferred examples of such are column chromatography using a cation-exchange resin or porous resin, which follows column chromatography using an anion-exchange resin for removing saccharides such as D-glucose. Examples of the desired anion-exchange resins to remove saccharides such as D-glucose include "AMBERLITE IRA411S" and "AMBERLITE IRA478RF" (both of which are commercialized by Rohm & Hass Company, Philadelphia, USA); and "DIAION WA30" (commercialized by Mitsubishi Chemical Corp., Tokyo, Japan). Examples of the desired cation-exchange resins to separate ascorbic acid 2-glucoside from L-ascorbic acid include "DOWEX 50WX8" (commercialized by Dow Chemical Co., Midland, USA); "AMBERLITE CG120" (commercialized by Rohm & Hass Company, Philadelphia, USA); "XT-1022E" (commercialized by Tokyo Organic Chemical Industries, Ltd., Tokyo, Japan); and "DIAION SK104" and "DIAION UBK 550" (both of which are commercialized by Mitsubishi Chemical Corp., Tokyo, Japan). Examples of the desired porous resins include "TOYOPEARL HW-40" (commercialized by Tosoh Corp., Tokyo, Japan); and "CELLFINE GH-25" (commercialized by Chico Corp., Tokyo, Japan). In the case of conducting column chromatography using cation-exchange resins or porous resins, preferable conditions are as follows: The solid concentration of a material solution to be fed to column is about 10% to about 50%, the load volume to a resin is about $1/1,000$- to $1/20$-fold of a wet resin volume, and refined water in an amount roughly equal to the wet resin volume is fed at a linear velocity of 0.5 to 5 m/hour. Among which, in the case of using a simulated-moving-bed column chromatography as the column chromatography using a cation-exchange resin, such column chromatography is preferable because it increases the purity of ascorbic acid 2-glucoside in the resulting purified product and reduces concomitants such as L-ascorbic acid and D-glucose, particularly, it reduces the L-ascorbic acid content and forms a particulate composition containing anhydrous crystalline ascorbic acid 2-glucoside with an L-ascorbic acid content of 0.1% or lower, d.s.b. For reference, varying depending on an operation temperature/setting flow rate, preferable elution conditions for simulated-moving-bed column chromatography, where a cation-exchange resin is used as a packing material, areas follows: The concentration of a solution, containing ascorbic acid 2-glucoside fed to the above column chromatography, is 60% or lower, the load volume of ascorbic acid 2-glucoside containing solution is $1/20$-fold by volume or lower of the wet resin volume, and the volume of refined water used as an eluent is not more than 30-folds by volume, usually, 5- to 20-folds by volume of the above load volume.

When the content of ascorbic acid 2-glucoside in the solution is 86% or lower, d.s.b., it is difficult to obtain a particulate composition containing anhydrous crystalline ascorbic acid 2-glucoside having either a degree of crystallinity of 90% or higher for anhydrous crystalline ascorbic acid 2-glucoside or a dynamic vapor sorption level of 0.01% or lower of the particulate composition, even when treated with the successive Steps (3) to (5). The reason is speculated that, when the content of ascorbic acid 2-glucoside in the solution is 86% or lower, d.s.b., the purity of ascorbic acid 2-glucoside in the resulting particulate composition containing anhydrous crystalline ascorbic acid 2-glucoside obtained through the subsequent steps is relatively low and this hinders the smooth crystallization thereof.

The solution purified up to give an ascorbic acid 2-glucoside content of over 86%, preferably, 88% or higher, d.s.b., is concentrated to give a prescribed concentration, usually, a concentration of about 65 to about 85% of ascorbic acid 2-glucoside, prior to the crystallization step of anhydrous crystalline ascorbic acid 2-glucoside. The concentrate is usually controlled to have a temperature of about 30 to about 45° C. The concentrate, having the concentration and the temperature, corresponds to ascorbic acid 2-glucoside containing solution with a saturation degree of 1.05 to 1.50.

<Step (3)>

Step (3) is for crystallizing ascorbic acid 2-glucoside from a solution containing over 86%, preferably, 88% or higher, d.s.b., of ascorbic acid 2-glucoside into anhydrous crystalline ascorbic acid 2-glucoside; the solution containing ascorbic acid 2-glucoside, previously purified and concentrated to give a prescribed purity and concentration and controlled to a prescribed temperature in Step (2), is transferred to a crystallizer, admixed with 0.1 to 5% of a seed crystal of anhydrous crystalline ascorbic acid 2-glucoside, and stirred gently, followed by gradually cooling the temperature of the solution to 5 to 20° C. over 6 to 48 hours to crystallize ascorbic acid 2-glucoside to form anhydrous crystalline ascorbic acid 2-glucoside. When a seed crystal of anhydrous crystalline ascorbic acid 2-glucoside is already present in the crystallizer, etc., there is no need of particularly adding such a seed crystal. At all events, crystallization of anhydrous crystalline ascorbic acid 2-glucoside from the above concentrate is preferably effected in the presence of such seed crystal. If necessary, concentration of the purified solution and crystallization of anhydrous crystalline ascorbic acid 2-glucoside in the solution can be simultaneously carried out in such a manner of boiling process.

<Step (4)>

Step (4) is for collecting the crystallized anhydrous crystalline ascorbic acid 2-glucoside; the massecuite is collected from the crystallizer and then anhydrous crystalline ascorbic acid 2-glucoside is collected by centrifugation.

<Step (5)>

Step (5) is for ageing the collected anhydrous crystalline ascorbic acid 2-glucoside and drying the resultant and optionally pulverizing the dried product; the anhydrous crystalline ascorbic acid 2-glucoside collected by centrifugation is washed with a small amount of refined water such as deionized water and distilled water to wash off the impurities adsorbed on the surfaces of crystals. The amount of water used for washing should not specifically be restricted, however, an excessive amount of which dissolves the crystals per se, as well as the impurities, resulting in a reduction of the production yield and an increment of cost for washing. Therefore, the surfaces of the crystals are usually, preferably washed with water in an amount of up to 30%, preferably, 15 to 25% of the weight of the crystals. The washing is preferably conducted under a centrifugal force in such a manner of placing crystals in a basket-type centrifuge. The crystals thus collected and washed are aged and dried by keeping them in an atmosphere with a predetermined temperature and humidity for a prescribed period of time to make the resulting crystals into a particulate composition with a degree of crystallinity of 90% or higher for anhydrous crystalline ascorbic acid 2-glucoside or a dynamic vapor sorption level of 0.01% or lower.

Although the product temperature of the particulate composition containing crystals in the ageing and drying steps, the relative humidity of the atmosphere, and the time for ageing and drying should not specifically be restricted as long as a particulate composition with the desired degree of crystallinity or dynamic vapor sorption level is obtained. However, the product temperature and the atmosphere should respectively, preferably be kept at a temperature of 20 to 55° C. and at a relative humidity of 60 to 90% in the ageing and drying steps. The total time for the ageing and drying steps is preferably about 5 to about 24 hours. The particulate composition containing crystals, obtained through the ageing and drying steps, is unforcedly cooled to an ambient temperature into a particulate composition containing anhydrous crystalline ascorbic acid 2-glucoside with a degree of crystallinity of 90% or higher for anhydrous crystalline ascorbic acid 2-glucoside or a dynamic vapor sorption level of 0.01% or lower. The crystalline particulate composition thus obtained is made into a final product with or without optional pulverization.

Except for the production yield of ascorbic acid 2-glucoside in the above Step (1) and the content of ascorbic acid 2-glucoside of any of the solutions in the above Steps (2) and (3), the above Steps (1) to (5) are basically the same as the production steps for quasi-drug-grade powders and they are free from any steps for recrystallization and for repeated washing of crystals, which are both indispensable in the production process of reagent grade powders.

The particulate composition containing anhydrous crystalline ascorbic acid 2-glucoside thus obtained is quite promptly made into a substantially non-hygroscopic particulate composition with an improved free-flowing ability by unforced cooling after ageing and drying steps, however, the degree of crystallinity for anhydrous crystalline ascorbic acid 2-glucoside does not increase to 90% or higher and the dynamic vapor sorption level of the particulate composition does not lower to 0.01% or lower, when the unforced cooling time is too short. When a particulate composition, prepared with short unforced cooling time, is directly made into a final product, only obtained is a particulate composition which possibly solidifies under normal storage circumstances similarly as quasi-drug-grade powders. Being influenced by the atmospheric temperature and humidity and also varying depending on the scale and structure of apparatuses/facilities used for drying, the possible shortest unforced cooling time requisite for obtaining the hardly, solidifiable particulate composition of the present invention is considered to be almost constant under constant conditions. Thus, when the relationship between (i) the unforced cooling time requisite for adjusting the degree of crystallinity to 90% or higher for anhydrous crystalline ascorbic acid 2-glucoside and adjusting the dynamic vapor sor when it has even option level of a particulate composition thereof to 0.01% or lower, and (ii) the atmospheric temperature and humidity, is once examined, upon specific apparatuses and facilities for actual use, there is no need in each case for examining the degree of crystallinity and the dynamic vapor sorption level of a particulate composition at every time of production, but the particulate composition of the present invention can be obtained by using the above unforced cooling time as the index.

The present inventors further found that, in place of unforced cooling of the particulate composition containing crystals after the above-identified ageing and drying, for example, a forced cooling by blowing a clean air with an about ambient temperature to the particulate composition to lower the temperature to around ambient temperature smoothly proceeds the crystallization of anhydrous crystalline ascorbic acid 2-glucoside into a particulate composition with a degree of crystallinity of 90% or higher for anhydrous crystalline ascorbic acid 2-glucoside and a dynamic vapor sorption level of 0.01% or lower in a relatively short period of time. The blowing air preferably has a temperature ranging from about 15 to about 30° C., more preferably, 18 to 28° C. In addition, the blowing time is usually, preferably about 5 to about 60 min, more preferably, 10 to 30 min. Varying depending on the temperature of blowing air, the effect of forced cooling is not so clearly observed with a blowing time of less than five minutes, while an improved increment in the degree of crystallinity is not expected even with a blowing time of over 60 min, and thus such blowing time is not preferable. In the case of blowing air, the cooling effect should preferably be exerted throughout the whole particulate composition containing crystals either by appropriately stirring or vibrating the particulate composition.

The particulate composition containing anhydrous crystalline ascorbic acid 2-glucoside thus obtained is of the present invention, which contains ascorbic acid 2-glucoside in an amount of over 98.0% but less than 99.9%, d.s.b., and either has a degree of crystallinity of 90% or higher for anhydrous crystalline ascorbic acid 2-glucoside, when calculated based on a profile of powder X-ray diffraction analysis of the particulate composition, or has a dynamic vapor sorption level of 0.01% or lower, when kept at 25° C. under a relative humidity of 35% for 12 hours after removal of free water from the particulate composition under nitrogen gas stream. Comparing to conventional quasi-drug-grade powders, the particulate composition is a significantly, hardly solidifiable particulate composition containing anhydrous crystalline ascorbic acid 2-glucoside, even under the conditions where the conventional powders will solidify.

In parentheses, solidification of materials has a fear of variously affecting production plants. For example, in the field of a food production where powderous materials are used, such materials are frequently, finely pulverized by roll crushers, air-transported to production lines by air-blowing, and transported by zigzag coil-conveyors. In such occasions, if the powderous materials were solidified, the following troublesome events will be induced: The rolls of roll crushers may be injured or burned, or sieves and transportation tubes installed in production lines may be blocked. Also solidified powderous materials have a high risk of causing operational troublesome events in their dissolution and in their mixing or kneading with other materials. Troubles in production steps caused by solidification of such powders are described in detail, for example, in "*Funryutai-Trouble-Shooting*" (Trouble shooting of powderous particles), edited by Tsutomu Shibata, published by Kogyo Chosakai Publishing Co., Ltd., Tokyo, Japan, pp. 15-19, 2006.

Since the particulate composition containing anhydrous crystalline ascorbic acid 2-glucoside of the present invention is significantly, hardly solidifiable compared to conventional quasi-drug-grade powders, it has an advantageous merit that it can be incorporated into one or more other powderous materials for food products, cosmetics, quasi-drugs, and pharmaceuticals in the field of manufactures of food products including beverages, as well as of cosmetics, quasi-drugs, and pharmaceuticals, which are produced in production plants that are designed where materials with satisfactory free-flowing ability will be used on the premises.

Examples of the above-identified powderous materials for food products include grain flours, starches, powdered sugars, powdered seasonings, powdered spices, powdered juices, powdered fats and oils, powdered peptides, powdered egg yolks, powdered milk, skim milk powders, powdered coffees, powdered cocoas, powdered miso, and powdered vegetables. Examples of powderous materials for cosmetics include face powders, talc, kaolin, mica, sericite, starches, bentonite, silk powders, cellulose powders, nylon powders, bath salts, soap tips, titanium dioxide, silicon dioxide (silica), and zinc oxide. Examples of powderous materials for quasi-drugs include amino acid salts, vitamin preparations, calcium preparations, excipients, fillers, fungicides, and enzyme preparations. Examples of powderous materials for pharmaceuticals include powdered effective ingredients; excipients and fillers such as oligosaccharides, lactose, starches, dextrins, white sugars, crystalline celluloses, sucrose esters, and fatty acid esters; and coating agents such as shellac. The particulate compositions containing anhydrous crystalline ascorbic acid 2-glucoside thus obtained usually contain L-ascorbic acid and/or D-glucose and have a reducing power of the whole particulate composition being less than one percent. In detail, they are satisfactory particulate compositions in that, while usually containing either or both of L-ascorbic acid and D-glucose in a detectable level by analytical methods such as high-performance liquid chromatography, specifically, in an amount of 0.01% or higher but not higher than 0.2%, d.s.b., they have a reducing power of the whole particulate composition being less than one percent, and therefore, as shown in the later described Experiment, they are substantially free of fear of causing discoloration (browning) even when heated in the presence of a compound(s) with amino group intramolecularly, such as amino acids and proteins. Preferably, the particulate compositions containing anhydrous crystalline ascorbic acid 2-glucoside thus obtained contains L-ascorbic acid in an amount of 0.1% or lower. When a particulate composition containing anhydrous crystalline ascorbic acid 2-glucoside has an L-ascorbic acid content of as low as 0.1% or lower, there is no fear of discloration in the particulate composition per se, even when stored for a relatively long period of time in the same product form as conventional quasi-drug-grade powders.

Further, the particulate compositions containing anhydrous crystalline ascorbic acid 2-glucoside thus obtained can be prepared alone into products of particulate compositions containing anhydrous crystalline ascorbic acid 2-glucoside because they usually contain particles with a particle size of less than 150 μm in an amount of 70% or more to each of the whole particulate compositions and those with a particle size of at least 53 μm but less than 150 μm in an amount of 40 to 60% to each of the whole particulate compositions. In the case of containing a relatively large amount of powderous particles with a particle size of larger than the above identified particles or having a particle distribution differing from the desired levels, they are appropriately pulverized to reduce their particle size or classified by sieving or the like to control their particle size.

The following experiments concretely explain the present invention:

EXPERIMENT 1

Influence of the Degree of Crystallinity on the Solidification of a Particulate Composition Containing Anhydrous Crystalline Ascorbic Acid 2-Glucoside Particulate compositions, containing anhydrous crystalline ascorbic acid 2-glucoside with different degrees of crystallinity for anhydrous crystalline ascorbic acid 2-glucoside in the range of 0 to 100%, were prepared and tested for solidification to examine the relationship between the degree of crystallinity and the solidifiability. The details are as follows:

EXPERIMENT 1-1

Preparation of Samples

<Test Sample No. 1>

"ASCORBIC ACID 2-GLUCOSIDE 999" (Code No. AG124, a purity of 99.9% or higher), a particulate composition containing anhydrous crystalline ascorbic acid 2-glucoside, as a standard sample consisting substantially of anhydrous crystalline ascorbic acid 2-glucoside, was used as test sample No. 1.

<Test Sample No. 2>

A particulate composition, prepared by dissolving test sample No. 1 in an adequate amount of refined water, freeze-drying the resulting solution for three days, and drying the resultant in vacuo under a temperature of 40° C. or lower overnight, was used as another standard sample consisting substantially of amorphous ascorbic acid 2-glucoside and was called "test sample No. 2". Test sample No. 2 had a moisture content of 2.0% when measured on Karl Fischer method.

<Test Sample Nos. 3 and 4>

As test sample Nos. 3 and 4 with a degree of crystallinity for anhydrous crystalline ascorbic acid 2-glucoside being between those of test sample Nos. 1 and 2, the following samples were prepared as follows: A particulate composition consisting of amorphous ascorbic acid 2-glucoside similarly prepared as the method for test sample No. 2 was spread over within a metallic tray and partially crystallized by keeping in a chamber with a constant temperature and humidity controlled at a temperature of 25° C. and a relative humidity of 90% for 24 or 72 hours to accelerate the crystallization. Successively, the metallic tray was taken out from the chamber, dried in vacuo at 38° C. overnight to obtain two types of particulate compositions, wherein the one with a keeping time of 24 hours in the temperature- and humidity-controlled chamber was called "test sample No. 3", while the other with a keeping time of 72 hours was called "test sample No. 4". Test sample Nos. 3 and 4 were respectively enclosed in a vial sealed with a cap and preserved with a desiccant in a desiccator under a sealed condition until just before subjecting to test for analysis.

EXPERIMENT 1-2

Purities of Ascorbic Acid 2-Glucoside and Degrees of Crystallinity of Test Sample Nos. 1 to 4

<Purity of Ascorbic Acid 2-Glucoside>

The purities of ascorbic acid 2-glucoside of test sample Nos. 1 to 4 were determined as follows: Using refined water, each of the test samples was made into a 2% aqueous solution, which was then filtered with a 0.45 μm membrane filter. The filtrate was subjected to high-performance liquid chromatography (HPLC) under the following conditions, followed by calculating the purity of ascorbic acid 2-glucoside, d.s.b., of each of the test samples based on the peak area of each refractive index chromatogram. The results are in Table 1.

Analytical Conditions

HPLC system: "LC-10AD", commercialized by Shimadzu Corp., Kyoto, Japan;

Degasser: "DGU-12AM", commercialized by Shimadzu Corp., Kyoto, Japan;

Column: "WAKOPAK WAKOBEADS T-330", $H^+$-form, commercialized by Wako Pure Chemical Industries, Osaka, Japan;

Sample injection volume: 10 µl;

Eluent: 0.01% (v/v) aqueous nitric acid solution;

Flow rate: 0.5 ml/min;

Temperature: 25° C.;

Refractive index detector: "RID-10A", commercialized by Shimadzu Corp., Kyoto, Japan;

Data processing apparatus: "CHROMATOPAK C-R7A", commercialized by Shimadzu Corp., Kyoto, Japan;

<Degree of Crystallinity>

The degrees of crystallinity of test sample Nos. 1 to for anhydrous crystalline ascorbic acid 2-glucoside were determined by: Subjecting each test sample to the analysis using "X' Pert PRO MPD", a product name of a commercially available reflected-light powder X-ray diffractometer commercialized by Spectris Co., Ltd., Tokyo, Japan; irradiating a CuKα-ray (X-ray electric current: 40 mA, electric voltage: 45 kV, wavelength: 1.5405 Å), as a characteristic X-ray irradiated from Cu target, to the sample to obtain a powder X-ray diffraction profile; and determining the analytical value for the degree of crystallinity of each of test sample Nos. 1 to 4 by Harmans' method using a Harmans' method computer software exclusively installed in the diffractometer. Prior to the above analysis, the particle degree and the bending factor pre-set in the software were respectively adjusted to appropriate levels for obtaining a base-line judged to be most preferable, while considering mutually overlapping peaks, diffraction intensity, and scattering intensity in respective powder X-ray diffraction patterns. The Harmans' method is described in detail in P. H. Harmans and A. Weidinger, "*Journal of Applied Physics*, Vol. 19, pp. 491-506 (1948) and P. H. Harmans and A. Weidinger, "*Journal of Polymer Science*", Vol. 4, pp. 135-144 (1949).

The degree of crystallinity of each test sample was calculated by substituting the following data into the above Formula 1: Hs as the value of degree of crystallinity of each test sample; $H_{100}$, the analytical value of that of test sample No. 1; and $H_0$, the analytical value of that of test sample No. 2. When analyzed by Harmans' method, the analytical value of the degree of crystallinity of test sample No. 1 (analytical value $H_{100}$) and that of test sample No. 2 (analytical value $H_0$) were respectively 70.23% and 7.57%. The results are also in Table 1. The powder X-ray diffraction patterns of test sample Nos. 1 and 2, as standard samples, are respectively shown in FIGS. 1 and 2.

Figure 1:
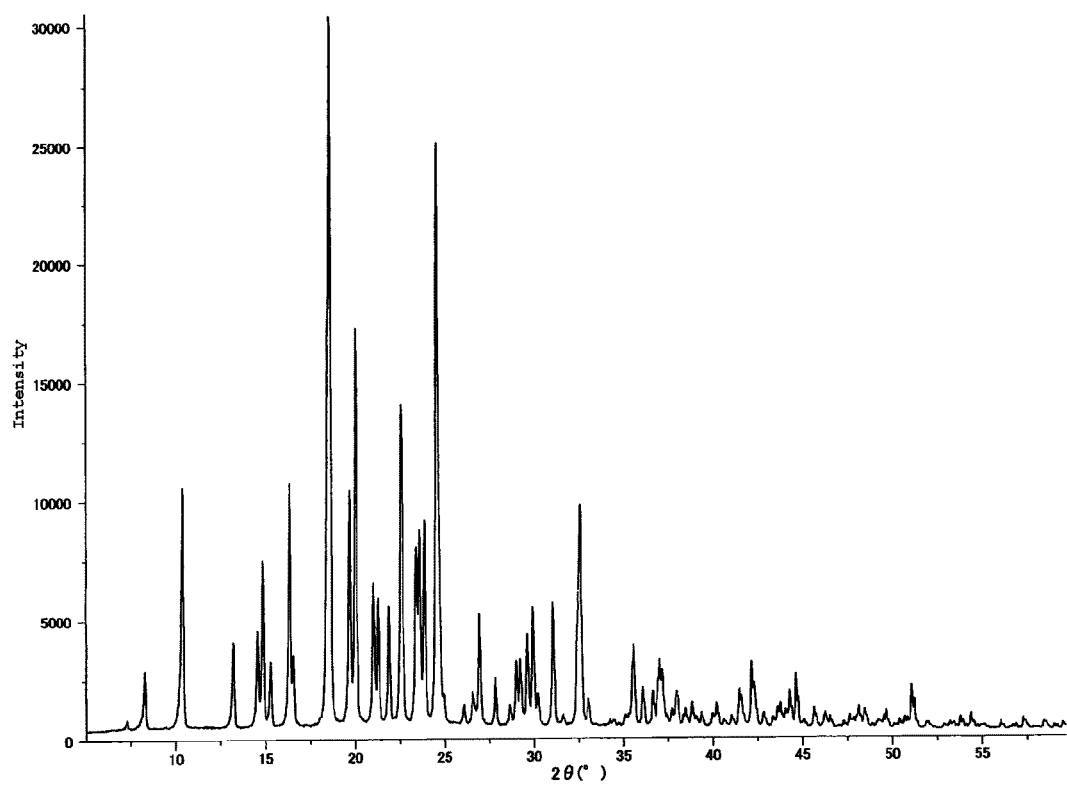
FIG. 1 is an example of powder X-ray diffraction pattern with a characteristic X-ray for a particulate composition containing anhydrous crystalline ascorbic acid 2-glucoside, which substantially consists of anhydrous crystalline ascorbic acid 2-glucoside.
Figure 2:
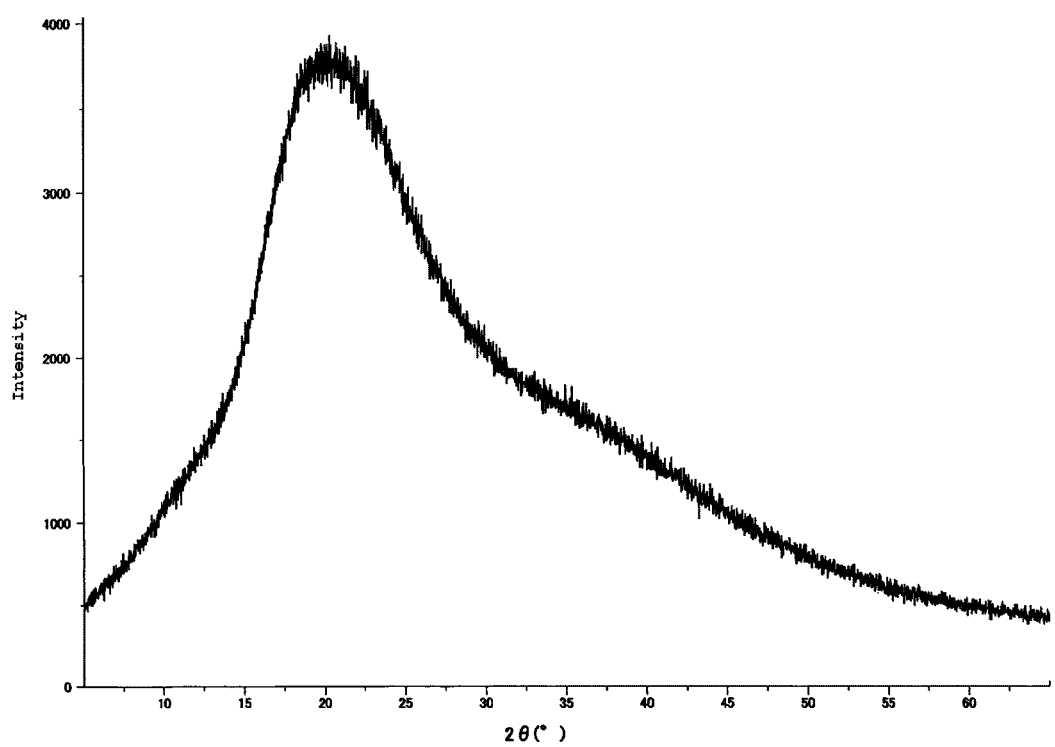
FIG. 2 is an example of powder X-ray diffraction pattern with a characteristic X-ray for a particulate composition containing ascorbic acid 2-glucoside, which substantially consists of amorphous ascorbic acid 2-glucoside.

As shown in FIG. 1, clear and sharp diffraction peaks specific to anhydrous crystalline ascorbic acid 2-glucoside were found in the range of diffraction angles (2θ) 4 to 65° in the powder X-ray diffraction pattern of test sample No. 1, but not any halo specific to amorphous ascorbic acid 2-glucoside was found. While, as shown in FIG. 2, unlike the powder X-ray diffraction pattern of FIG. 1, halo specific to amorphous ascorbic acid 2-glucoside was clearly found as a bunchy baseline in the powder X-ray diffraction pattern of test sample No. 2, but not any diffraction peak specific to anhydrous crystalline ascorbic acid 2-glucoside was found.

EXPERIMENT 1-3

Powder X-Ray Diffraction Analyses of Test Sample Nos. 1 and 2 Using a Synchrotron Radiation This experiment was carried out to further confirm that test sample Nos. 1 and 2 were proper standard samples for determining the analytical values $H_{100}$ and $H_0$. These samples were subjected to a transmitted-light powder X-ray diffractometry, which detects a weak diffraction and scattering, using a synchrotron radiation (called "radiation", hereinafter), as an X-ray radiation source. The analytical conditions were as follows.

<Analytical Conditions>

Powder X-ray diffractometer: Model "PDS-16", a high-speed powder X-ray diffractometer (Debye Scherrer mode, camera length: 497.2 mm) commercialized by Kohzu Precision Co., Ltd., Kanagawa, Japan;

X-ray radiation source: "Beam line of Hyogo Prefecture (BL08B2)", radiation from defecting electromagnet;

Wavelength: 0.7717 Å (16.066 keV);

Strength: $10^9$ photons/sec;

Measuring angle: 2 to 40°;

Exposure time: 600 sec;

Image recording: "IMAGING PLATE BAS-2040", an imaging plate commercialized by Fujifilm Corp., Tokyo, Japan; and Image analyzer: "BIO-IMAGE ANALYZER BAS-2500", commercialized by Fujifilm Corp., Tokyo, Japan.

The measurement was conducted by using "Beam line of Hyogo Prefecture (BL08B2)" placed at "SPring-8", a synchrotron radiation facility, 1-1-1 Koto, Sayo-cho, Sayo, Hyogo, Japan.

Prior to the powder X-ray diffraction analysis, test sample Nos. 1 and 2 were respectively ground in a mortar and sieved with a 53 µm mesh-sieve. Then, each of the resulting particulate compositions passed through the sieve was homogeneously injected into "MARKTUBE No. 14", a product name of a glass capillary for powder X-ray diffraction (diameter: 0.6 mm, Lindeman glass), commercialized by Toho KK, Tokyo, Japan, to give an injected sample length of about 30 mm. Successively, the capillary was cut at the end terminal of the injected sample and the open end was sealed with an adhesive. Then, the capillary was fixed on a sample mount with a clay, and the sample mount was set to the powder X-ray diffractometer to give the longitudinal direction of the capillary perpendicularly against the optic axis of the powder X-ray diffractometer.

To remove adverse effect of the orientation of anhydrous crystalline ascorbic acid 2-glucoside on the powder X-ray diffraction profile, the measurement of the powder X-ray diffraction was carried out by allowing the sample mount to reciprocate at a uniform velocity toward the longitudinal direction of the capillary in a width of ±1.5 mm and at a time cycle of once/60 sec, and simultaneously allowing the sample mount to rotate at a uniform velocity around the rotational axis in the longitudinal direction of the capillary at a time cycle of twice/sec.

In the processes of analyzing the powder X-ray diffraction profiles and preparing the powder X-ray diffraction patterns of test sample Nos. 1 and 2, background signals inherent to the powder X-ray diffractometer were eliminated from each powder X-ray diffraction profile according to conventional manner for improving the measurement accuracy. The resulting powder X-ray diffraction patterns of test sample Nos. 1 and 2 are shown in FIGS. 3 and 4, respectively.

Figure 3:
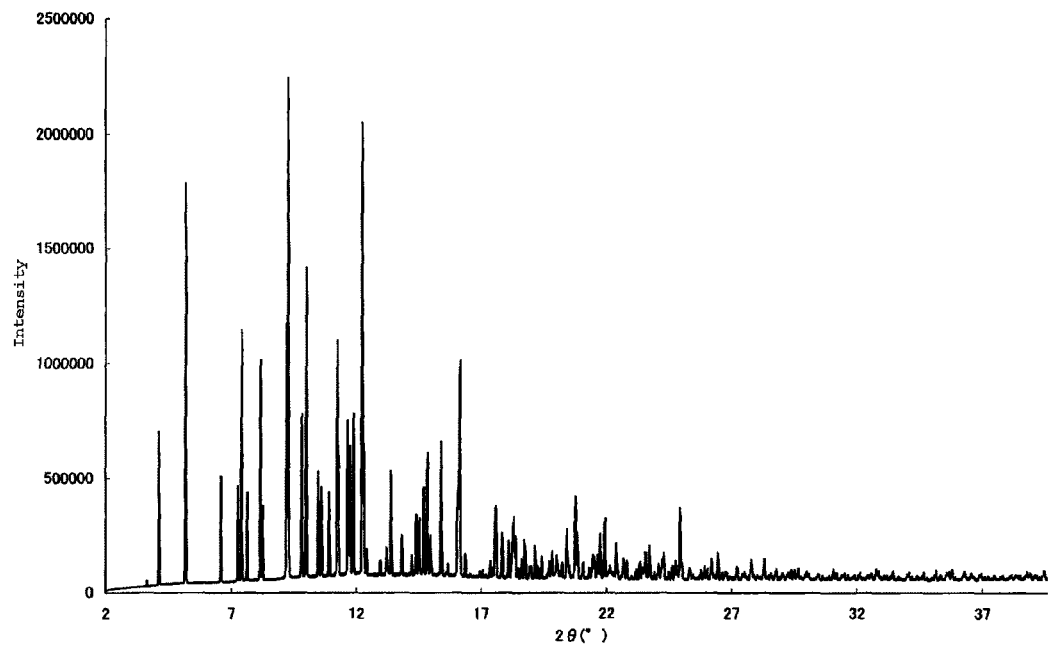
FIG. 3 is an example of powder X-ray diffraction pattern with a synchrotron radiation for a particulate composition containing anhydrous crystalline ascorbic acid 2-glucoside, which substantially consists of anhydrous crystalline ascorbic acid 2-glucoside.

As shown in FIG. 3, the diffraction peaks specific to anhydrous crystalline ascorbic acid 2-glucoside appeared clearly and sharply in the range of diffraction angles (2θ) of 2 to 40° for the powder X-ray diffraction pattern of test sample No. 1, measured by using the synchrotron radiation. Since the wavelength of synchrotron radiation (0.7717 Å) was different from that of characteristic X-ray (1.5405 Å), each diffraction peak in FIG. 3 appeared by about a half diffraction angle (2θ) of each of the corresponding peaks in FIG. 1. However, the powder X-ray diffraction patterns in FIGS. 1 and 3 were extremely well coincided with each other. While, the peak width at half height of each diffraction peak in FIG. 3 was evidently narrower than that in FIG. 1, and each diffraction peak in FIG. 3 showed higher resolution than that in FIG. 1, although the peak strength in FIG. 3 was higher by nearly 100-folds than that in FIG. 1. The powder X-ray diffraction pattern in FIG. 3 showed no halo specific to amorphous ascorbic acid 2-glucoside, as shown in the following FIG. 4. The result indicates that the degree of crystallinity of test sample No. 1 for anhydrous crystalline ascorbic acid 2-glucoside is extremely high, and test sample No. 1 substantially consists of anhydrous crystalline ascorbic acid 2-glucoside.

Figure 4:
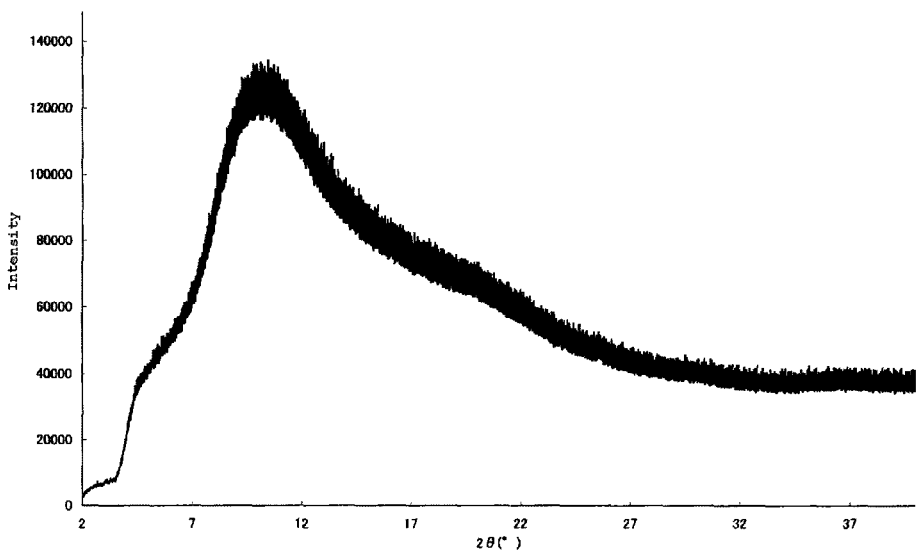
FIG. 4 is an example of powder X-ray diffraction pattern with a synchrotron radiation for a particulate composition containing ascorbic acid 2-glucoside, which substantially consists of amorphous ascorbic acid 2-glucoside.

As shown in FIG. 4, the powder X-ray diffraction pattern of test sample No. 2, obtained by using the synchrotron radiation, showed a remarkable halo specific to amorphous ascorbic acid 2-glucoside as a bunchy baseline but not any diffraction peak specific to anhydrous crystalline ascorbic acid 2-glucoside. This result indicates that test sample No. 2 consists substantially of amorphous ascorbic acid 2-glucoside.

The above results, obtained by using the synchrotron radiation as an X-ray source, support that test sample Nos. 1 and 2 are proper standard samples for defining the analytical values $H_{100}$ and $H_0$, respectively, for use in Formula 1.

EXPERIMENT 1-4

Solidification Test

The following experiment was to investigate the solidification property of respective test sample Nos. 1 to 4: One gram each of the test sample Nos. 1 to 4, prepared in Experiment 1-1, was separately placed in "FALCON TUBE 2059", a product name of a 14-ml polypropylene cylindrical tube (1.7 cm in diameter, 10 cm in height) having a hemispherical bottom shape and a cap, commercialized by Becton, Dickinson and Company, New Jersey, USA. The tubes were set to a tube rack uprightly and allowed to stand for 24 hours, after the tube rack was placed in "IC-410", a product name of an incubator commercialized Advantec Toyo Kaisha, Ltd., Tokyo, Japan, controlled at 50° C. After the incubation, the tubes were taken out from the incubator, followed by removing each cap, taking out each sample from each tube to place it on a black-plastic-plane plate by turning the tubes upside down slowly, and macroscopically observing the conditions of the samples.

The degree of solidification of each test sample was judged based on the following criteria:

"Solidified", (+): Sample clearly kept the hemispherical shape of the bottom of the tube even on the plate;
"Slightly solidified", (±): Sample slightly showed the hemispherical shape of the bottom of the tube;
"Not solidified", (−): Sample deformed and showed no hemispherical shape of the bottom of the tube. The results were shown in the column of "Solidifiability" of Table 1.

TABLE 1

| | Test sample No. | | | |
|---|---|---|---|---|
| | 1 | 2 | 3 | 4 |
| Purity of ascorbic acid 2-glucoside (%) | 99.9 | 99.1 | 99.1 | 99.1 |
| Degree of crystallinity (%) | 100.0 | 0.0 | 88.3 | 93.1 |
| Solidification | − | + | + | − |

As shown in Table 1, test sample No. 1, as a standard sample for defining the analytical value $H_{100}$ (degree of crystallinity: 100.0%), was judged to be "Not solidified" (−) because it easily collapsed and did not keep the hemispherical shape of the bottom of the tube, when taken out from the tube and placed on a plane plate. In contrast, test sample No. 2 as another standard sample for defining the analytical value $H_0$ (degree of crystallinity: 0.0%) was judged to be "Solidified" (+) because it still kept the hemispherical shape of the bottom of the tube when taken out from the tube and placed on the plate. The hemispherical shape of test sample No. 2 did not collapsed even when a slight vibration was given to the plate.

Test sample No. 3 with a degree of crystallinity of 88.3% kept the hemispherical shape of the bottom of the tube, even when taken out from the tube and placed on the plate, and it was clearly judged to be "Solidified" (+), similar to test sample No. 2. Test sample No. 4 with a degree of crystallinity of 93.1% collapsed same as test sample No. 1, however, lost its shape and collapsed just after having been taken out from the tube and placed on the plate and judged to be "Not solidified" (−).

As described above, although test sample Nos. 2 to 4 were prepared from test sample No. 1 with an ascorbic acid 2-glucoside purity of 99.9%, the above-mentioned HPLC analysis showed that their purities of ascorbic acid 2-glucoside were not increased to a level higher than 99.1%. The reason of this is not clear but it can be speculated that a slight amount of ascorbic acid 2-glucoside might be lost by degradation or the like during preparation.

From the above results, in the case of particulate compositions containing 99.1% or higher, d.s.b., of anhydrous crystalline ascorbic acid 2-glucoside, those with a higher degree of crystallinity for anhydrous crystalline ascorbic acid 2-glucoside tend to have a lower solidifiability; and the facts that test sample No. 3 with a degree of crystallinity of 88.3% was judged to be "Solidified" (+) and test sample No. 4 with a degree of crystallinity of 93.1% was judged to be "Not solidified" (−) indicate that a threshold changing from the judgment of "Solidified" (+) to that of "Not solidified" (−) under the above solidification test lies between a degree of crystallinity of 88.3% and 93.1%.

EXPERIMENT 2

Relationship Between the Solidification and the Degree of Crystallinity of a Particulate Composition Containing Anhydrous Crystalline Ascorbic Acid 2-Glucoside In this experiment, based on the results in Experiment 1, seven types of particulate compositions containing anhydrous crystalline ascorbic acid 2-glucoside, having a degree of crystallinity for anhydrous crystalline ascorbic acid 2-glucoside in the range of 0 to 100% and a purity of ascorbic acid 2-glucoside in the range of 99.1 to 99.9%, were used and tested for solidifiability similarly as in Experiment 1 to investigate the relationship between the solidification and the degree of crystallinity in more detail.

EXPERIMENT 2-1

Preparation of Test Sample

Particulate compositions of test sample Nos. 5 to 9 in Table 2 were prepared by weighing test sample Nos. 1 and 2, which had been prepared in Experiment 1-1, in appropriate amounts, respectively, and mixing them to homogeneity. Table 2 shows the purities of ascorbic acid 2-glucoside and the degrees of crystallinity for anhydrous crystalline ascorbic acid 2-glucoside of test sample Nos. 5 to 9, determined by the method disclosed in Experiment 1-2. The results of test sample Nos. 1 and 2 in Table 2 were copied from Table 1.

EXPERIMENT 2-2

Solidification Test

Test sample Nos. 5 to 9 were subjected to the solidification test in Experiment 1-4. The results are shown in the column of "Solidification" in Table 2. The results of solidification of test sample Nos. 1 and 2 in Table 2 were copied from Table 1.

TABLE 2

| | Test sample No. | | | | | | |
|---|---|---|---|---|---|---|---|
| | 1 | 2 | 5 | 6 | 7 | 8 | 9 |
| Purity of ascorbic acid 2-glucoside (%) | 99.9 | 99.1 | 99.8 | 99.7 | 99.6 | 99.5 | 99.4 |
| Degree of crystallinity (%) | 100.0 | 0.0 | 99.8 | 92.6 | 91.5 | 89.2 | 29.9 |
| Solidification | − | + | − | − | − | ± | + |

As found in the results of Table 2, test sample No. 9 with a degree of crystallinity of 29.9% was judged to be "Solidified" (+) and test sample No. 8 with a degree of crystallinity of 89.2% was judged to be "Slightly solidified" (±). In contrast, test sample Nos. 7, 6 and 5 with respective degrees of crystallinity of 91.5%, 92.6%, and 99.8% were judged to be "Not solidified" (−) similar to test sample No. 1. These results indicate that, among particulate compositions containing anhydrous crystalline ascorbic acid 2-glucoside, which contains ascorbic acid 2-glucoside in an amount of 99.1% or higher but less than 99.9%, d.s.b., those with a degree of crystallinity of 90% or higher for anhydrous crystalline ascorbic acid 2-glucoside do not solidify under the conditions of this experiment.

EXPERIMENT 3

Influence of the Dynamic Vapor Sorption Level on the Solidification of Particulate Composition Containing Anhydrous Crystalline Ascorbic Acid 2-Glucoside Since the hygroscopicity of a particulate composition containing anhydrous crystalline ascorbic acid 2-glucoside is estimated to be involved in the solidification of the particulate composition, in this experiment, the dynamic vapor sorption level, which is assumed to be a useful index for estimating hygroscopicity, of test sample Nos. 1 and 2 and test sample Nos. 5 to 9 were measured and the effect of dynamic vapor sorption level on the solidification of particulate compositions containing anhydrous crystalline ascorbic acid 2-glucoside was investigated by verifying the results of solidification test obtained in Experiment 2-2.

EXPERIMENT 3-1

Measurement for Dynamic Vapor Sorption Level

About 50 mg aliquots of respective test sample Nos. 1 and 2, prepared in Experiment 1-1, and test sample Nos. 5 to 9, prepared in Experiment 2-1, were respectively placed in a mesh sample bucket and allowed to stand in "IGA SORP", a dynamic vapor sorption apparatus commercialized by Hiden Isocheme Corp., while the mesh sample buckets were set to sample holders (made of stainless steel). The test samples were dehydrated by keeping at a temperature of 25° C. and a relative humidity of 0% for 12 hours under nitrogen gas stream at a flow rate of 200 ml/min and promptly weighed. Further, the test samples were kept at a temperature of 25° C. and a relative humidity of 35% for 12 hours under nitrogen gas stream and weighed again. Dynamic vapor sorption level (%) of each test sample was calculated by substituting into the aforesaid Formula 2 the weight of each test sample whose moisture has been eliminated and the weight of the same sample just after hydrated at a temperature of 25° C. and a relative humidity of 35% for 12 hours. The data of dynamic vapor sorption levels of test sample Nos. 1 and 2 as well as test sample Nos. 5 to 9, obtained in this experiment, are shown in Table 3. In parallel, the purities of ascorbic acid 2-glucoside, obtained in Experiment 2-1, and the test results on solidification thereof, obtained in Experiment 2-2, are shown in Table 3.

TABLE 3

| | Test sample No. | | | | | | |
|---|---|---|---|---|---|---|---|
| | 1 | 2 | 5 | 6 | 7 | 8 | 9 |
| Purity of ascorbic acid 2-glucoside (%) | 99.9 | 99.1 | 99.8 | 99.7 | 99.6 | 99.5 | 99.4 |
| Dynamic vapor sorption level (%) | <0.01 | 1.70 | <0.01 | <0.01 | 0.01 | 0.05 | 0.13 |
| Solidification | − | + | − | − | − | ± | + |

As shown in Table 3, the dynamic vapor sorption levels of test sample Nos. 2 and 5 to 9 were varied from less than 0.01% (corresponding to "<0.01" in Table 3 and this applies hereinafter), i.e., a value of lower than detection limit, to 1.70%, and this indicates that even particulate compositions containing anhydrous crystalline ascorbic acid 2-glucoside, which contains ascorbic acid 2-glucoside in an amount of 99.1% or higher but less than 99.9%, d.s.b., may have significantly different dynamic vapor sorption levels. Every test sample Nos. 1, 5 and 6 had a dynamic vapor sorption level of lower than detection limit. On the contrary, test sample Nos. 2, 8 and 9 had a dynamic vapor sorption level of over 0.05%, particularly, test sample No. 2 had a dynamic vapor sorption level of 1.70%, a 10-fold higher dynamic vapor sorption level than those of test sample Nos. 8 and 9.

Comparing the above results and the results of the column of "Solidification" in Table 3, there exists a clear correlation between the solidification of particulate compositions containing anhydrous crystalline ascorbic acid 2-glucoside and their dynamic vapor sorption levels; test sample Nos. 1, 5, 6 and 7, having a dynamic vapor sorption level of lower than detection limit or as low as 0.01%, were judged to be "Not solidified" (−), while test sample Nos. 2, 8 and 9, having a dynamic vapor sorption level reaching 0.05 to 1.70%, were judged to be "Solidified" (+) or "Slightly solidified" (±). The results of this experiment indicate that, in addition to the degree of crystallinity, the dynamic vapor sorption level of a particulate composition containing anhydrous crystalline ascorbic acid 2-glucoside must be a useful index for realizing a hardly solidifiable one. The above results also indicate that a particulate composition containing anhydrous crystalline ascorbic acid 2-glucoside with an ascorbic acid 2-glucoside content of 99.1% or higher but less than 99.9%, d.s.b., and with a dynamic vapor sorption level of 0.01% or lower, is not solidified under the conditions of this experiment.

The fact that test sample No. 2 showed a distinctly high dynamic vapor sorption level as high as 1.70% in this experiment suggests that the vapor sorption is mainly induced by amorphous ascorbic acid 2-glucoside. On the other hand, the fact that test sample No. 1 showed a dynamic vapor sorption level of lower than detection limit suggests that the sample does not substantially contain amorphous ascorbic acid 2-glucoside like test sample No. 2. These results well coincided with the powder X-ray diffraction patterns of test sample No. 1 shown in FIGS. 1 and 3 and they support that test sample No. 1 is a proper standard sample for defining the analytical value $H_{100}$ for anhydrous crystalline ascorbic acid 2-glucoside, as a basis for calculating the degree of crystallinity for anhydrous crystalline ascorbic acid 2-glucoside according to Formula 1.

EXPERIMENT 4

Influence of Forced Cooling on the Degree of Crystallinity, Dynamic Vapor Sorption Level, and Solidification of Particulate Composition From the results of the foregoing experiments, it was revealed that, in a particulate composition containing anhydrous crystalline ascorbic acid 2-glucoside, both the degree of crystallinity and the dynamic vapor sorption level of the particulate composition closely relate to the solidification thereof. Accordingly, in this experiment, the following were examined; the influence of forced cooling of a particulate composition containing crystals after ageing and drying steps in the production thereof on the degree of crystallinity, the dynamic vapor sorption level, and the solidification of a particulate composition containing anhydrous crystalline ascorbic acid 2-glucoside.

EXPERIMENT 4-1

Preparation of Test Sample

Particulate compositions, prepared similarly as in test sample No. 2 in Experiment 1-1, were respectively spread on a metallic tray and kept in a chamber with a constant temperature and humidity controlled at 25° C. and a relative humidity of 90% for 16 hours to accelerate crystallization and to partially crystallize the resulting particulate composition. Thereafter, the metallic tray was taken out from the chamber, dried at 40° C. for eight hours, and successively, unforcedly cooled for about two hours to obtain test sample No. 10 or cooled by force after drying and then blowing 20° C. air for 15 or 40 min to the particulate composition in the tray to obtain test sample Nos. 11 and 12, respectively. Test sample Nos. 10 to 12 were respectively enclosed hermetically in a vial with a cap and stored in a desiccator with a desiccant until just before being subjected to analytical tests.

EXPERIMENT 4-2

Measurement of the Purity of Ascorbic Acid 2-Glucoside

The purities of ascorbic acid 2-glucoside of test sample Nos. 10 to 12 were measured by the method described in Experiment 1-2 and the results are in Table 4. The purity of ascorbic acid 2-glucoside of test sample No. 1 was copied from Table 1.

EXPERIMENT 4-3

Measurement of the Degree of Crystallinity and Dynamic Vapor Sorption Level

The degree of crystallinity for anhydrous crystalline ascorbic acid 2-glucoside and the dynamic vapor sorption levels of the particulate compositions of test sample Nos. 10 to 12 were measured by the methods described in Experiments 1 and 3, respectively. The results are in Table 4. The results for test sample No. 1 in Table 4 were copied from Tables 1 and 3.

EXPERIMENT 4-4

Solidification Test

Test sample Nos. 10 to 12 were subjected to the solidification test as in Experiment 1-4. The results are shown in the column of "Solidification" in Table 4 along with the result of that of test sample No. 1 described in Table 1.

TABLE 4

|  | Test sample No. | | | |
| --- | --- | --- | --- | --- |
|  | 1 | 10 | 11 | 12 |
| Purity of ascorbic acid 2-glucoside (%) | 99.9 | 99.1 | 99.1 | 99.1 |
| Cooling condition for crystalline powder | — | Unforced cooling | Blowing 20° C. air for 15 min | Blowing 20° C. air for 40 min |
| Degree of crystallinity (%) | 100.0 | 88.1 | 91.5 | 94.1 |
| Dynamic vapor sorption level (%) | <0.01 | 0.06 | <0.01 | <0.01 |
| Solidification | − | + | − | − |

As evident from Table 4, test sample No. 10, prepared by unforced cooling after ageing and drying steps of a particulate composition containing anhydrous crystalline ascorbic acid 2-glucoside obtained by crystallization, had a degree of crystallinity of 88.1% for anhydrous crystalline ascorbic acid 2-glucoside and a dynamic vapor sorption level of 0.06%, and it was judged to be "Solidified" (+) by the solidification test. On the contrary, test sample No. 11, prepared through forced cooling by blowing 20° C. air for 15 min after ageing and drying a particulate composition containing anhydrous crystalline ascorbic acid 2-glucoside, had a degree of crystallinity 91.5% for anhydrous crystalline ascorbic acid 2-glucoside and a dynamic vapor sorption level of lower than detection limit, and it was judged to be "Not solidified" (−) by the solidification test. Similarly, test sample No. 12, prepared through forced cooling by blowing 20° C. air for 40 min after ageing and drying a particulate composition containing anhydrous crystalline ascorbic acid 2-glucoside, had a degree of crystallinity of 94.1% for anhydrous crystalline ascorbic acid 2-glucoside and a dynamic vapor sorption level of lower than detection limit, and it was judged to be "Not solidified" (−) by the solidification test. These results indicate that the crystallization of a particulate composition can be promoted by forced cooling rather than unforced cooling conducted after ageing and drying steps of a particulate composition, meaning that the forced cooling is more advantageous than unforced cooling in preparing a particulate composition with a higher degree of crystallinity for anhydrous crystalline ascorbic acid 2-glucoside and a lower dynamic vapor sorption level, i.e., a hardly solidifiable particulate composition.

EXPERIMENT 5

Influence of the Purity of Ascorbic Acid 2-Glucoside on the Solidification of a Particulate Composition Containing Anhydrous Crystalline Ascorbic Acid 2-Glucoside From the above experiments, it was revealed that, in a particulate composition containing anhydrous crystalline ascorbic acid 2-glucoside with an ascorbic acid 2-glucoside purity as high as 99.1% or higher, both the degree of crystallinity for anhydrous crystalline ascorbic acid 2-glucoside and the dynamic vapor sorption level respectively, closely relate to the solidification of the particulate composition. In this experiment, the relationship between the solidification of the particulate composition and the purity of L-ascorbic acid thereof was further investigated.

EXPERIMENT 5-1

Preparation of Test Sample

Test sample Nos. 13 to 18, shown in Table 5, having different purities of ascorbic acid 2-glucoside, were prepared from aqueous solutions containing L-ascorbic acid and dextrin, a kind of amylaceous substance, as described below; and subjected to the solidification test similarly as in Experiment 1-4.

Four parts by weight of "PINEDEX #100", a dextrin commercialized by Matsutani Chemical Industries Co., Ltd., Hyogo, Japan, was dissolved in 15 parts by weight of water by heating. Then, three parts by weight of L-ascorbic acid was admixed with the solution. Successively, 100 units/g dextrin of CGTase from *Geobacillus stearothermophilus* Tc-62 strain and 250 units/g dextrin of isoamylase, commercialized by Hayashibara Biochemical Laboratories Inc., Okayama, Japan, were admixed with the above solution and subjected to an enzymatic reaction while keeping the resulting solution at a pH of 5.5 and a temperature of 55° C. for 50 hours to form ascorbic acid 2-glucoside. It can be speculated that α-glycosyl-L-ascorbic acids such as 2-O-α-maltosyl-L-ascorbic acid, 2-O-α-maltotriosyl-L-ascorbic acid, 2-O-α-maltotetraosyl-L-ascorbic acid, etc., must be formed in the reaction solution.

After inactivating the enzymes by heating, the reaction solution was adjusted to pH 4.5, admixed with 50 units/g-dextrin of "GLUCZYME AF6", a product name of a glucoamylase specimen commercialized by Amano Enzymes Inc., Aichi, Japan, and subjected to an enzymatic reaction for 24 hours for hydrolyzing the above α-glycosyl-L-ascorbic acids into ascorbic acid 2-glucoside and hydrolyzing the remaining concomitant oligosaccharides into D-glucose. After the reaction, the reaction solution contained ascorbic acid 2-glucoside in a production yield of 39%.

The reaction solution was heated to inactivate glucoamylase, decolored and filtered with an activated charcoal, subjected to a column of cation-exchange resin ($H^+$-form) for desalting and then subjected to an anion-exchange resin ($OH^-$-form) to absorb L-ascorbic acid and ascorbic acid 2-glucoside, followed washing the resin with water to remove D-glucose and feeding 0.5 N hydrochloric acid solution to effect elution. The eluate was concentrated to give a solid content of about 50% and then subjected to column chromatography using "DOWEX 50WX4" ($Ca^{2+}$-form), a product name of a strong-acid cation exchange resin commercialized by Dow Chemical Company. The eluate concentrated to give a solid content of about 50% was loaded on the column in a volume of about 1/50-fold of the wet resin volume in the column, and fed with refined water in a volume of 50-folds of the load volume of the eluate at a linear velocity of 1 m/hour, followed by fractionating the resulting eluate by 0.05-volume aliquots of the column volume. Thereafter, the composition of each fraction was measured on HPLC described in Experiment 1-1, and six fractions with an ascorbic acid 2-glucoside content of 80%, d.s.b., or higher were collected, and concentrated in vacuo to give a solid concentration of about 76%. The resulting concentrate was placed in a crystallizer, admixed with test sample No. 1, obtained in Experiment 1-1, as a seed, in an amount of two percent of the solid contents, d.s.b., followed by cooling the temperature of the solution from 40° C. to 15° C. over two days under gentle stirring conditions to crystallize ascorbic acid 2-glucoside to form anhydrous crystalline ascorbic acid 2-glucoside.

Thereafter, according to conventional manner, test sample Nos. 13 to 18, shown in Table 5, were prepared by collecting crystals from the massecuite by a basket-type centrifuge, washing the crystals with a small amount of distilled water, ageing and drying the washed crystals, blowing 25° C. air for 30 min to the aged and dried crystals for cooling, and pulverizing the resultant.

TABLE 5

|  | Test sample No. | | | | | | | | |
| --- | --- | --- | --- | --- | --- | --- | --- | --- | --- |
|  | 1 | 2 | 13 | 14 | 15 | 16 | 17 | 18 | 19 |
| Purity of ascorbic acid 2-glucoside (%) | 99.9 | 99.1 | 97.4 | 98.0 | 98.6 | 99.1 | 99.5 | 99.7 | 98.9 |
| Degree of crystallinity (%) | 100.0 | 0.0 | 88.7 | 89.0 | 91.6 | 94.8 | 99.4 | 99.5 | 88.9 |
| Dynamic vapor sorption level (%) | <0.01 | 1.70 | 0.07 | 0.04 | 0.01 | <0.01 | <0.01 | <0.01 | 0.03 |
| Solidification | − | + | + | ± | − | − | − | − | ± |
| Storage stability | − | − | + | + | − | − | − | − | + |

Test sample Nos. 1 and 2 in Table 5 were the same as those in Experiment 1-1, and the purities of ascorbic acid 2-glucoside, the degrees of crystallinity for anhydrous crystalline ascorbic acid 2-glucoside, and the dynamic vapor sorption levels thereof were copied from the antecedent experimental results. In addition, "AA2G", a product name of a particulate composition containing anhydrous crystalline ascorbic acid 2-glucoside, commercialized by Hayashibara Biochemical Laboratories, Inc., Okayama, Japan, which is a conventional quasi-drug-grade powder, was used as test sample No. 19. According to the methods described in the antecedent experiments, the purities of ascorbic acid 2-glucoside, the degrees of crystallinity for anhydrous crystalline ascorbic acid 2-glucoside, and the dynamic vapor sorption levels of test sample Nos. 13 to 19 were measured, and the results are in Table 5.

EXPERIMENT 5-2

Solidification Test

Test sample Nos. 13 to 19, obtained in Experiment 5-1, were tested for their solidification by the similar method as in Experiment 1-4. The results are shown in Table 5. The results of the solidification tests for test sample Nos. 1 and 2 in Table 5 were copied from Table 1.

EXPERIMENT 5-3

Test for Storage Stability

To confirm that the solidification test conducted in Experiment 1-4, etc., is a proper test for evaluating the solidifiability of a particulate composition containing anhydrous crystalline ascorbic acid 2-glucoside under practical storage conditions, test sample No. 1 obtained in Experiment 1-1, test sample Nos. 13 to 18 obtained in Experiment 5-1, and test sample No. 19 were subjected to a storage stability test which is designed taking account of conditions, environment, and period of time of actual storage of a particulate composition containing anhydrous crystalline ascorbic acid 2-glucoside.

Ten kilograms aliquots of any of test sample Nos. 1 and 13 to 19 were respectively placed in a polyethylene-double-bag (80 mm by 600 mm). Then, each bag was placed in a 18-liter steel can in such a manner of allowing the opening part of the bag to stand upright and to be opened, allowing to stand without capping the steel can, and storing for 45 days under the conditions of ambient temperature and free of moisture control. After 45-days storage, each polyethylene bag with any of the test samples was taken out from the can, and the test samples were taken out from the bags and placed on a black plastic plane plate for macroscopic observation of their free-flowing abilities and solidification degrees.

The test samples were judged about their solidification by the following criteria: "Solidified" (+); cake(s) is/are detected in a test sample and the free-flowing ability of the test sample has lowered in comparison with that at the initiation of the test. "Not solidified" (−); no cake is detected in a test sample and the free-flowing ability of the test sample has not changed in comparison with that at the initiation of the test. The storage form of each test sample in the storage stability test is the same as those of quasi-drug-grade powders, when they are commercially distributed and stored, except for not closing the opening of the bag with a rubber band, not putting in any desiccant, and not being stored in a steel can with a cover thereupon. The above three differences were provided for the purpose of setting the environments for storage test slightly harder than those of the practical commercial distribution and storage conditions of the particulate compositions. The results are also in Table 5.

As shown in Table 5, except for test sample No. 2 consisting substantially of amorphous ascorbic acid 2-glucoside and test sample No. 19, a quasi-drug-grade powder, the remaining test sample Nos. 1 and 13 to 18 tend to increase their degrees of crystallinity for anhydrous crystalline ascorbic acid 2-glucoside as their purities of ascorbic acid 2-glucoside increase. In the solidification test, test sample Nos. 13 and 14 with respective purities of ascorbic acid 2-glucoside of 97.4% and 98.0% were judged to be "Solidified" (+) or "Slightly solidified" (±). On the contrary, test sample Nos. 15 to 18 with a purity of ascorbic acid 2-glucoside of 98.6 to 99.7% were judged to be "Not solidified" (−). These results indicate that the threshold value of the purity of ascorbic acid 2-glucoside that influences on the solidifiability lies at around 98.0% and this concludes that the purity of ascorbic acid 2-glucoside being over 98.0% must be needed for obtaining a particulate composition containing anhydrous crystalline ascorbic acid 2-glucoside which is judged to be "Not solidified" (−) by the solidification test.

No solidification was observed in test sample Nos. 15 to 18 similarly as in test sample 1, though the purities of ascorbic acid 2-glucoside of test sample Nos. 15 to 18 were 98.6% to 99.7%, which were almost the same levels as that of test sample No. 19, a quasi-drug-grade powder, with a purity of 98.9%, and significantly lower than that of test sample No. 1, a reagent grade powder consisting substantially of anhydrous crystalline ascorbic acid 2-glucoside. For reference, the degrees of crystallinity for anhydrous crystalline ascorbic acid 2-glucoside of test sample Nos. 15 to 18 were 91.6% to 99.5%, and test sample No. 19, a quasi-drug-grade powder, had 88.9% as low as less than 90%. From these results, it can be concluded that the degree of crystallinity for anhydrous crystalline ascorbic acid 2-glucoside should be made 90% or higher for obtaining a desired particulate composition, containing anhydrous crystalline ascorbic acid 2-glucoside which is significantly solidifiable than test sample No. 19, a quasi-drug-grade powder.

In test sample Nos. 1 and 13 to 18, there was found a tendency that their dynamic vapor sorption levels decrease as their purities of ascorbic acid 2-glucoside increase. Test sample No. 13 with a dynamic vapor sorption level of 0.07% was judged to be "Solidified" (+), and Sample 14 and 19 with respective dynamic vapor sorption levels of 0.04% and 0.03% were judged to be "Slightly solidified" (±). On the contrary, test sample No. 15 with a dynamic vapor sorption level of 0.01% and test sample Nos. 16 to 18 with dynamic vapor sorption levels of lower than detection limit were judged to be "Not solidified" (−). These results indicate that the dynamic vapor sorption level of a particulate composition containing anhydrous crystalline ascorbic acid 2-glucoside should be made 0.01% or lower to obtain a particulate composition containing anhydrous crystalline ascorbic acid 2-glucoside which has a significantly lower solidifiability than test sample No. 19, a quasi-drug-grade powder.

As shown in the bottom column of Table 5, test sample Nos. 13 and 14 with respective purities of ascorbic acid 2-glucoside of 97.4% and 98.0% were judged to be "Solidified" (+) on the storage stability test, in which they were stored for 45 days in bags in respective amounts of 10 kg/bag along the lines of their actually commercialized products form. On the contrary, test sample Nos. 15 to 18 with a purity of ascorbic acid 2-glucoside of 98.6% to 99.7% were judged to be "Not solidified" (−) similar to the results in their solidification tests. These facts indicate that the solidification test as shown in Experiment 1-4, etc., is a proper test for evaluating the solidification of a particulate composition containing anhydrous crystalline ascorbic acid 2-glucoside under practical storage circumstances.

EXPERIMENT 6

Relationship Between the Degree of Crystallinity and the Crystallite Size of Particulate Composition Containing Anhydrous Crystalline Ascorbic Acid 2-Glucoside In general, a powderous particle of a powder containing crystals is considered to be constructed by plural single crystal, i.e., constructed by crystallites. It is speculated that the higher the degree of crystallinity of a powder, the larger the size (diameter) of each crystallite becomes. The above crystallite size is said to be calculated based on "Scherrer formula" shown in the following Formula [6] by using a half-width of a diffraction peak and a diffraction angle, which are calculated based on powder X-ray diffraction profiles. A computer software for calculating such crystallite size is installed in a general powder X-ray diffraction analyzer. Test sample No. 1, consisting substantially of anhydrous crystalline ascorbic acid 2-glucoside, prepared in Experiment 1; test sample No. 15, a particulate composition containing anhydrous crystalline ascorbic acid 2-glucoside prepared in Experiment 5 and having a purity of ascorbic acid 2-glucoside and a degree of crystallinity for its anhydrous crystalline form, which are relatively close to those of conventional quasi-drug-grade powders; and test sample No. 19 used in Experiment 5, a conventional quasi-drug-grade powder, were selected and calculated for crystallite size of a single powderous particle by the following method:

$$D = \frac{K\lambda}{\beta \cos\theta} \quad \text{Formula [6]}$$

D: Size of crystallite (Å)
λ: Wavelength of X-ray (Å)
β: Diffraction line width (rad)
θ: Diffraction angle(°)
K: Constant (0.9 when a half-width (a full-width at half maximum) is used for β)

<Method for Calculating Crystallite Size of Anhydrous Crystalline Ascorbic Acid 2-Glucoside>

The power X-ray diffraction profiles, which had been used for determining the analytical values for the anhydrous crystalline ascorbic acid 2-glucosides in respective test sample Nos. 1, 15 and 19 in Experiment 1 or 5, were used as powder X-ray diffraction profiles for the basis of calculating crystallite size. From the diffraction patterns prepared by analyzing the above powder X-ray diffraction profiles, diffraction peaks with diffraction angles (2θ) of around 10.4°, 13.2°, 18.3°, 21.9° and 22.6° were selected as diffraction peaks which are used for calculating the crystallite size of an anhydrous crystalline ascorbic acid 2-glucoside and are separable each other in a region at a relatively lower angle that is recognized to have a lesser influence on diffraction peak width arisen from non-uniform strain of crystallite in a powderous particle. Using "X' pert Highscore Plus", an analytical processing computer software installed in a powder X-ray diffraction analyzer, the powder X-ray diffraction profiles of respective test samples were processed to determine the half-widths and diffraction angles (2θ) of the selected five diffraction peaks, which were then calibrated based on the measurements obtained with, as a standard, silicon ("Si640C", an X-ray diffraction standard sample, provided by National Institute of Standards and Technology (NIST) in USA. With the calibrated half-widths and diffraction angles (2θ), the crystallite size of anhydrous crystalline ascorbic acid 2-glucoside in each test sample was calculated by the program of "Scherrer" formula in the computer software. The results are in Table 6.

The crystallite size of each test sample was an average of the calculated data from the selected five diffraction peaks, respectively. The purity of ascorbic acid 2-glucoside and the degree of crystallinity of anhydrous crystal thereof are only copied from those in Table 5. For reference, since the powder X-ray diffraction patterns of test sample Nos. 15 and 19 were both detected at diffraction angles (2θ) in the range of 4° to 65° as clear and sharp diffraction peaks characteristic to anhydrous crystalline ascorbic acid 2-glucoside and the diffraction patterns were well coincided with the powder X-ray diffraction pattern (FIG. 1) of test sample No. 1, it was judged reasonable to compare the test samples each other based on their calculated data for crystallite size of anhydrous crystalline ascorbic acid 2-glucoside contained in each test sample, based on the powder X-ray diffraction patterns of these test samples.

TABLE 6

|  | Test sample No. | | |
| --- | --- | --- | --- |
|  | 1 | 15 | 19 |
| Purity of ascorbic acid 2-glucoside (%) | 99.9 | 98.6 | 98.9 |
| Degree of crystallinity (%) | 100 | 91.6 | 88.9 |
| Crystallite size (Å) | 1,770 | 1,440 | 1,380 |

As found in Table 6, the crystallite size of anhydrous crystalline ascorbic acid 2-glucoside of test sample No. 1 with a degree of crystallization of 100% for anhydrous crystalline ascorbic acid 2-glucoside was calculated to be 1,770 Å. The crystallite size of anhydrous crystalline ascorbic acid 2-glucoside of test sample No. 15 with a degree of crystallization of 91.6% for anhydrous crystalline ascorbic acid 2-glucoside was calculated to be 1,440 Å. In addition, the crystallite size of anhydrous crystalline ascorbic acid 2-glucoside of test sample No. 19 with a degree of crystallization of 88.9% for anhydrous crystalline ascorbic acid 2-glucoside was calculated to be 1,380 Å. The higher the degree of crystallinity of anhydrous crystalline ascorbic acid 2-glucoside, the larger the crystallite size becomes, and this reveals that, among these three types of test samples, there is a relationship between the degree of crystallinity and the crystallite size.

EXPERIMENT 7

Relationship Between the Reducing Power and the Browning of Particulate Composition Containing Anhydrous Crystalline Ascorbic Acid 2-Glucoside The test samples used in the above experiments were all particulate compositions containing anhydrous crystalline ascorbic acid 2-glucoside prepared from solutions containing ascorbic acid 2-glucoside obtained through a step of allowing CGTase to act on solutions containing L-ascorbic acid and amylaceous substance. When employed such production process, the resulting particulate compositions will contain L-ascorbic acid and D-glucose as concomitants specific to the production process regardless of the amount of such concomitants. Since both L-ascorbic acid and D-glucose have reducibility, particulate compositions containing anhydrous crystalline ascorbic acid 2-glucoside, varying depending on the amount of L-ascorbic acid and D-glucose, may possibly cause disadvantageous browning (coloration) in the final products when used in products containing compounds with an amino group, such as proteins and amino acids. In particular, since L-ascorbic acid has a relatively high reactivity with oxygen, it is speculated that L-ascorbic acid must be a causative of inducing not only unfavorable coloration in products containing it but also a causative of the coloration of conventional quasi-drug-grade powders in themselves, which were conventionally observed occasionally when the conventional quasi-drug-grade powders were stored for a relatively long period of time.

Accordingly, in this experiment, test sample Nos. 1 and 15 to 19, which had been used in the antecedent Experiments, were examined for the relationship between the total content of L-ascorbic acid and D-glucose, L-ascorbic acid content, and the reducing power of the whole particulate composition and the coloration by an accelerated test of heat treatment according to the following procedures:

One hundred and fifty milligrams of each of test sample was weighed and placed in a 10-ml test tube with a screw cap, and the test tubes in a closed condition with the screw cap were placed in "DRYING-OVEN SA310", a product name of an oven commercialized by Masuda Corp., Osaka, Japan, and heated at 80° C. for three days. Subsequently, after removing the screw caps from the test tubes, three milliliters of deionized water was added to each of the tubes to dissolve the samples. The resulting solutions were measured for absorbance at 400 nm using "UV-2400PC", a product name of a spectrophotometer commercialized by Shimadzu Corp., Kyoto, Japan. The degree of coloration caused by heating was judged based on the following two criteria: When an absorbance at a wavelength of 400 nm is less than 0.50, it is judged to be "Not browned or substantially not browned" (−); and absorbance at a wavelength of 400 nm being 0.50 or higher, "Browned" (+). The results are in Table 7.

The total content of L-ascorbic acid and D-glucose in each test sample was determined on HPLC described in Experiment 1-1. The reducing power of the whole particulate composition of each test sample was determined by measuring the amounts of reducing sugars and total sugars by Somogyi-Nelson method and anthrone-sulfuric acid method generally used in the art, respectively, using D-glucose as a standard substance; and calculating the reducing power by substituting the data into the aforesaid Formula 3. The total content of L-ascorbic acid and D-glucose, the content of L-ascorbic acid, and the reducing power of the whole particulate composition for each sample are shown in Table 7.

TABLE 7

|  |  | Test sample No. |  |  |  |  |  |
|---|---|---|---|---|---|---|---|
|  |  | 1 | 15 | 16 | 17 | 18 | 19 |
| Composition (%), d.s.b. | Ascorbic acid 2-glucoside | 99.9 | 98.6 | 99.1 | 99.5 | 99.7 | 98.9 |
|  | Total content of L-ascorbic acid and D-glucose (L-ascorbic acid) | 0.0 (0.0) | 0.2 (0.1) | 0.1 (<0.1) | 0.1 (<0.1) | <0.1 (0.0) | 0.3 (0.2) |
|  | Others | 0.1 | 1.2 | 0.8 | 0.4 | 0.3 | 0.8 |
| Reducing power of the whole particulate composition (%) |  | 0.05 | 0.98 | 0.86 | 0.20 | 0.12 | 1.12 |
| Browning property |  | − | − | − | − | − | + |

As shown in Table 7, in particulate compositions containing anhydrous crystalline ascorbic acid 2-glucoside, the contents of L-ascorbic acid and D-glucose in test sample No. 1, a reagent grade powder substantially consisting of anhydrous crystalline ascorbic acid 2-glucoside were all as low as lower than their detection limits. On the contrary, L-ascorbic acid and/or D-glucose were detected in any of test sample Nos. 12 to 18 as the particulate compositions containing anhydrous crystalline ascorbic acid 2-glucoside of the present invention, and test sample No. 19, a conventional quasi-drug-grade powder. In such powders, as evident from test sample Nos. 15 to 18, those with a total content of L-ascorbic acid and D-glucose of not higher than 0.2%, d.s.b., were judged to be "Not browned or substantially not browned" (−); while as evident from test sample No. 19, that with a total content of L-ascorbic acid and D-glucose reaching 0.3%, d.s.b., was judged to be "Browned" (+). As for L-ascorbic acid which is considered to be more strongly related to the coloration of powders, as evident from test sample Nos. 15 to 18, when the total content of L-ascorbic acid and D-glucose is 0.2% or lower, d.s.b., they were judged to be "Not browned or substantially not browned" (−); while as evident from test sample No. 19, when the total content of L-ascorbic acid and D-glucose reaching 0.3%, d.s.b., it was judged to be "Browned" (+). For reference, as already mentioned, since L-ascorbic acid has a relatively high reactivity with oxygen and relates to the coloration of particulate compositions containing anhydrous crystalline ascorbic acid 2-glucoside, those with an L-ascorbic acid content of not higher than 0.1%, d.s.b., are beyond apprehension of causing coloration even when stored for a relatively long period of time in the product form of conventional quasi-drug-grade powders.

From the viewpoint of the reducing power, as evident from test sample Nos. 15 to 18, those with a reducing power of the whole particulate composition being less than one percent were judged to be "Not browned or substantially not browned" (−). On the contrary, as evident from test sample No. 19, test samples with a reducing power of the whole particulate composition being over one percent were judged to be "Browned" (+). These results were well coincident with the above results obtained by judgement with an index of the total content of L-ascorbic acid and D-glucose.

The above results indicate that particulate compositions containing anhydrous crystalline ascorbic acid 2-glucoside free of fear of causing coloration can be obtained by controlling their reducing powers of their whole particulate compositions to a level of less than one percent even though they inevitably contain L-ascorbic acid and/or D-glucose in a detectable level due to their production processes. Considering both the aspects of the coloration of not only the final products prepared with particulate compositions but also of the particulate compositions per se, the above results show that the content of L-ascorbic acid in particulate compositions should preferably be 0.1%, d.s.b., or lower.

The following examples explain the present invention in more detail, but the present invention should never be restricted thereby.

EXAMPLE 1

Preparation of Crude CGTase Solution

*Geobacillus stearothermophilus* Tc-62 strain (FERM BP-11143, a deposit number in National Institute of Bioscience and Human-Technology Agency of Industrial Science and Technology) was cultured with "NUTRIENT AGAR", a slant culture medium, commercialized by Difco Laboratories, Inc., at 50° C. for two days. One loop of the cultured cells, collected from the slant culture medium, was inoculated to a seed liquid medium, containing 2% of soluble starch, 0.5% of ammonium chloride, 0.05% of potassium hydrogen phosphate, 0.025% of magnesium sulfate, and 0.5% of calcium carbonate, cultured at 50° C. for three days with shaking. The resulting seed culture was inoculated to a main culture medium having the same composition as the seed culture medium except for replacing the soluble starch with dextrin, and further cultured at 50° C. for three days with shaking. The cells were removed from the resulting culture by centrifugation, and the resulting supernatant was concentrated with a UF-membrane up to give a volume of about 1/18 thereof to obtain a crude CGTase solution.

Preparation of Particulate Composition Containing Anhydrous Crystalline Ascorbic Acid 2-Glucoside Four parts by weight of liquefied potato starch was dissolved in 20 parts by weight of water by heating, and the solution was admixed with three parts by weight of L-ascorbic acid and adjusted to pH 5.5 for use as a substrate solution. The substrate solution was admixed with the above crude CGTase enzyme solution in an amount of 100 units/g solid of the liquefied potato starch and isoamylase produced by Hayashibara Co., Ltd., Okayama, Japan, in an amount of 250 units/g solid of the liquefied potato starch, and enzymatically reacted at 55° C. for 40 hours to form, along with ascorbic acid 2-glucoside, α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid.

After inactivating the enzyme by heating, the solution was adjusted to pH 4.5, admixed with "GLUCZYME AF6", a product name of a glucoamylase specimen (6,000 units/g), commercialized by Amano Enzyme, Inc., Aichi, Japan, in an amount of 50 units/g solid of the liquefied potato starch, and reacted at 55° C. for 24 hours to degrade α-glycosyl-L-ascorbic acids into ascorbic acid 2-glucoside and to degrade the concomitant saccharides into D-glucose. The production yield of ascorbic acid 2-glucoside in the reaction solution was about 39%. The reaction solution contained 5-O-α-glucosyl-L-ascorbic acid and 6-O-α-glucosyl-L-ascorbic acid in a total content of about 0.1%, d.s.b.

After inactivating the enzyme by heating, the solution was decolored and filtered with an activated charcoal, and the filtrate was desalted with a cation-exchange resin ($H^+$-form). Then, L-ascorbic acid and ascorbic acid 2-glucoside in the desalted solution were allowed to adsorb onto an anion-exchange resin ($OH^-$-form), washed with water to remove D-glucose, and eluted with 0.5 N hydrochloric acid solution. The eluate was concentrated to give a solid content concentration of about 50% and subjected to a simulated-moving-bed column chromatography using 10 columns packed with "DIAION UBK550" ($Na^+$-form), a product name of a strong-acid cation-exchange resin commercialized by Mitsubishi Chemical Corp., Tokyo, Japan. The eluate, which had been concentrated to give a solid content concentration of about 50%, was fed to the column in an amount of about 1/40-fold volume of the wet resin volume, and fed with an eluent in an amount of about 15-fold volumes of the volume fed to elute ascorbic acid 2-glucoside, followed by collecting a fraction rich in ascorbic acid 2-glucoside but poor in L-ascorbic acid. The fraction contained 92.2% of ascorbic acid 2-glucoside, d.s.b.

After the fraction was concentrated under a reduced pressure into an about 72% concentrate, which was then placed in a crystallizer and admixed with "ASCORBIC ACID 2-GLUCOSIDE 999" (code No.: AG124, a purity of ascorbic acid 2-glucoside of 99.9% or higher), a product name of a particulate composition containing anhydrous crystalline ascorbic acid 2-glucoside, commercialized as an analytical standard reagent by Hayashibara Biochemical Laboratories, Inc., Okayama, Japan, as a seed, in an amount of two percent of the solid contents. Then, the mixture solution was adjusted to 40° C. and gradually cooled to 15° C. over two days under gentle stirring conditions to crystallize ascorbic acid 2-glucoside to form anhydrous crystalline ascorbic acid 2-glucoside.

The crystals were collected by a basket-type centrifuge, washed by spraying a small amount of cold refined water, aged and dried at 38° C. for three hours, cooled by blowing 25° C. air for 45 min, and pulverized to obtain a particulate composition containing anhydrous crystalline ascorbic acid 2-glucoside, which had a purity of 99.5% of ascorbic acid 2-glucoside, a total content of 0.1% of L-ascorbic acid and D-glucose, a content of less than 0.1% of L-ascorbic acid, a degree of crystallinity of 97.0% for anhydrous crystalline ascorbic acid 2-glucoside, and a total reducing power of the whole particulate composition being 0.25%. The dynamic vapor sorption level of the particulate composition was lower than detection limit. When measured for particle distribution, the particulate composition contained particles with a particle size of less than 150 μm in an amount of 91.2% and those with a particle size of 53 μm or more but less than 150 μm in an amount of 50.2%. When subjected to the same solidification test and browning test as in Experiments 1-4 and 7, respectively, the particulate composition was judged to be "Not solidified" (−) in the solidification test and "Not browned or substantially not browned" (−) in the browning test.

The particulate composition is easily handleable because it hardly solidifies and has a lesser colorability as compared to "AA2G", a product name of a conventional quasi-drug-grade powder commercialized by Hayashibara Biochemical Laboratories, Inc., Okayama, Japan, commercialized conventionally as a skin-whitening ingredient in a grade for use in quasi-drugs, etc. Since the particulate composition does not differ from conventional quasi-drug-grade powders in that it is a particulate composition containing anhydrous crystalline ascorbic acid 2-glucoside, similarly as in the above conventional powders, it can be used alone or in combination with other ingredients as a powderous material for food products, cosmetics, quasi-drugs, pharmaceuticals, etc. Since it has an L-ascorbic acid content of 0.1% or lower, there is no fear of causing coloration in the particulate composition per se even when the composition is stored for a relatively long period of time in the same product form as conventional quasi-drug-grade powders.

EXAMPLE 2

Preparation of Crude CGTase Solution

A crude CGTase solution was prepared similarly as in Example 1 except for using *Geobacillus stearothermophilus* Tc-27 strain (FERM BP-11142, a deposit number in National Institute of Bioscience and Human-Technology Agency of Industrial Science and Technology) in place of *Geobacillus stearothermophilus* Tc-62 strain.

Preparation of Particulate Composition Containing Anhydrous Crystalline Ascorbic Acid 2-Glucoside Five parts by weight of corn starch was added to 15 parts by weight of water and then dissolved therein by heating after the addition of a commercialized liquefying enzyme. The resulting solution was admixed with three parts by weight of L-ascorbic acid and adjusted to pH 5.5 to give a substrate solution. To the substrate solution was added the above crude CGTase solution and isoamylase produced by Hayashibara Biochemical Laboratories, Inc., Okayama, Japan, in respective amounts of 100 units and 1,000 units/g solid of the corn starch, followed by an enzymatic reaction at 55° C. for hours to form ascorbic acid 2-glucoside and other α-glycosyl-L-ascorbic acids.

After inactivating the enzyme by heating, the reaction solution was adjusted to pH 4.5, admixed with "GLUCOZYME #20000", a product name of a glucoamylase specimen with an activity of 20,000 units/g, commercialized by Nagase ChemteX Corp., Osaka, Japan) in an amount of 50 units/g solid of the corn starch, and reacted at 55° C. for 24 hours to degrade α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic into ascorbic acid 2-glucoside; and to degrade the concomitant saccharides into D-glucose. The resulting reaction solution contained ascorbic acid 2-glucoside in a production yield of about 37%. Also, the reaction solution contained 5-O-α-glucosyl-L-ascorbic acid 6-O-α-glucosyl-L-ascorbic acid in a total amount of about 0.2%.

After inactivating the enzyme by heating, the reaction solution was decolored and filtered with an activated charcoal. The filtrate was desalted with a cation-exchange resin ($H^+$-form), and fed to an anion-exchange resin ($OH^-$-form) to adsorb L-ascorbic acid and ascorbic acid 2-glucoside thereupon, followed by washing the anion-exchange resin with water to remove D-glucose and feeding 0.5 N hydrochloric acid solution to the resin for elution. The eluate was fed to column chromatography using "TOYOPEARL HW-40", a product name of a porous resin of Tosoh Corp., Tokyo, Japan, to collect a fraction rich in ascorbic acid 2-glucoside but poor in L-ascorbic acid. The collected fraction contained 89.5%, d.s.b., of ascorbic acid 2-glucoside.

The fraction was concentrated in a reduced pressure into an about 76% concentrate, which was then placed in a crystallizer and admixed with the particulate composition containing anhydrous crystalline ascorbic acid 2-glucoside prepared in Example 1, as a seed, in an amount of two percent of the solid contents. Thereafter, the resulting mixture was heated to 40° C. and then gradually cooled to 15° C. over two days with gentle stirring to crystallize ascorbic acid 2-glucoside to form anhydrous crystalline ascorbic acid 2-glucoside.

The crystals were collected by using a basket-type centrifuge, washed by spraying a small amount of distilled water, ageing and drying the resultant at 35° C. for eight hours, cooling by blowing 25° C. air for 15 min to the resultant product, and pulverizing the cooled product to obtain a particulate composition containing anhydrous crystalline ascorbic acid 2-glucoside, which had a purity of 99.2% of ascorbic acid 2-glucoside, a total content of less than 0.1% of L-ascorbic acid and D-glucose, a content of less than 0.1% of L-ascorbic acid, a degree of crystallinity of 94.4% for anhydrous crystalline ascorbic acid 2-glucoside, and a total reducing power of the whole particulate composition being 0.15%. The particulate composition had a dynamic vapor sorption level of lower than detection limit. Measurement of the particle distribution of the particulate composition revealed that it contained particles with particle sizes of less than 150 µm in an amount of 83.2% and those with particle sizes of 53 µm or more but less than 150 µm in an amount of 57.1%. When subjected to the same solidification test and browning test as in Experiments 1-4 and 7, respectively, the particulate composition was judged to be "Not solidified" (−) in the solidification test and "Not browned or substantially not browned" (−) in the browning test.

The particulate composition is easily handleable because it hardly solidifies and has a lesser colorability as compared to conventional "AA2G", a product name of a particulate composition containing anhydrous crystalline ascorbic acid 2-glucoside commercialized by Hayashibara Biochemical Laboratories, Inc., Okayama, Japan, in a grade for use in quasi-drugs as a skin-whitening ingredient, etc. Since the particulate composition does not differ from conventional quasi-drug-grade powders in that it is a particulate composition containing anhydrous crystalline ascorbic acid 2-glucoside, it can be used alone or in combination with other ingredients as a material for food products, cosmetics, quasi-drugs, pharmaceuticals, etc., similarly as the above conventional powders. Since the particulate composition has an L-ascorbic acid content of 0.1% or lower, there is no fear of causing coloration in the particulate composition per se even when the composition is stored for a relatively long period of time in the same product form as conventional quasi-drug-grade powders.

EXAMPLE 3

Preparation of CGTase Mutant

The CGTase of *Geobacillus stearothermophilus* (known as *Bacillus stearothermophilus* in previous classification) Tc-91 strain was cloned its gene and determined its mature CGTase's amino acid sequence (SEQ ID NO: 1) based on the nucleotide sequence (SEQ ID NO: 2). The mature CGTase has been known to have in its amino acid sequence four conserved regions which had been recognized to commonly exist in the enzymes classified into the α-amylase family. The steric structure of the protein of CGTase has been already determined by X-ray crystallographic analysis and revealed to have four domains, A, B, C and D as shown in FIG. 5 (see "*Kogyo-yo-Toshitsu-Koso-Handbook*", pp. 56-63, Kodansha Scientific K. K. Ed., Tokyo, Japan (1999)). Three catalytic groups of the CGTase, i.e. $225^{th}$ aspartic acid (D225), $253^{rd}$ glutamic acid (E253), and $324^{th}$ aspartic acid (D324) of the amino acid sequence SEQ ID NO: 1 were identified (see "*Kogyo-yo-Toshitsu-Koso-Handbook*", pp. 56-63, Kodansha Scientific K. K. Ed., Tokyo, Japan (1999)). FIG. 6 is a schematic diagram of the primary structure of CGTase. By inducing a mutation in the DNA of CGTase gene by the following procedures, a CGTase mutant, which has a higher productivity of ascorbic acid 2-glucoside than that of the wild-type CGTase, was obtained.

The CGTase gene of *Geobacillus stearothermophilus* Tc-91 strain (deposited under the accession number of FERM P-2225 and under transferring procedure to International Deposit under the accession number of FERM ABP-11273 in International Patent Organism Depositary in National Institute of Advanced Industrial Science and Technology), maintained by the present inventors, was mutated by inducing or deleting cleavage sites of restriction enzymes without altering the amino acid sequence of the CGTase and recombined with a plasmid vector to make into a recombinant DNA containing the gene encoding the wild-type CGTase. The structure of the recombinant DNA, "pRSET-iBTC12", was shown in FIG. 7. Gene fragments (Nde I-EcoT22I fragments), containing a region encoding active site of the wild-type CGTase in the above recombinant DNA, were obtained by digesting the recombinant DNA, and randomly mutating the resultants in vitro using "GeneMorph PCR Mutagenesis Kit" (a product name of a PCR mutation kit commercialized by Stratagene Company). The mutated fragments were inserted into the original recombinant DNA to prepare gene mixtures, which encode CGTase variants with various amino acid replacements. Recombinant DNAs were obtained by recombining the variant genes with an expression plasmid vector. With the recombinant DNAs, coliform cells were transformed to obtain a gene library of the CGTase variants.

Over 13,000 strains of transformants were isolated from the gene library and cultured to obtain cells, and from which were prepared lysis solutions as crude enzymes containing CGTase variants. The crude enzymes were allowed to act on an aqueous solution containing L-ascorbic acid and partial starch hydrolysates to form α-glycosyl-L-ascorbic acids, which were then treated with glucoamylase to form ascorbic acid 2-glucoside. By comparing the production yields of α-glycosyl-L-ascorbic acids with that of the wild-type CGTase, transformants capable of producing a CGTase mutant having higher productivity of ascorbic acid 2-glucoside were screened. Consequently, a desired transformant having a gene of the desired CGTase mutant was obtained. The nucleotide sequence of the CGTase mutant gene of the transformant was decoded and revealed that the $228^{th}$ lysine residue in the amino acid sequence SEQ ID NO: 1 was replaced with glutamic acid residue.

The transformant containing the gene or the DNA encoding the above CGTase mutant was cultured with T-medium containing 100 μl/ml of sodium ampicillin (containing 12 g of Bacto-Trypton, 24 g of Bacto-Yeast Extract, 5 ml of glycerol, 17 mM monopotassium phosphate, and 72 mM dipotassium phosphate per L of the medium) at 37° C. for 24 hours under an aerobic condition. The cells collected from the culture by centrifugation were disrupted by "ULTRA SONIC HOMOGENIZER UH-600 (an ultrasonic disruptor produced by SMT Co., Ltd.), and the supernatant was treated by heating at 60° C. for 30 min to inactivate or denature the non-heat-resistant proteins inherent to the host cells. The heat-treated supernatant was further centrifuged to prepare a partially purified specimen of the CGTase mutant.

Preparation of Particulate Composition Containing Anhydrous Crystalline Ascorbic Acid 2-Glucoside Five parts by weight of potato starch was admixed with 15 parts by weight of water and then dissolved therein by heating after the addition of a commercialized starch-liquefying enzyme. The solution was admixed with three parts by weight of L-ascorbic acid and adjusted to pH 5.5 to give a substrate solution. The substrate solution was admixed with the partially purified CGTase mutant obtained by the above method in an amount of 20 units/g potato starch and reacted at 65° C. for 72 hours to form ascorbic acid 2-glucoside and α-glycosyl-L-ascorbic acids. Thereafter, the reaction was heated to inactivate the remaining CGTase mutant. To the solution was added "GLUCOZYME #20000" (a product name of a glucoamylase with an activity of 20,000 units/g commercialized by Nagase ChemteX Corp., Osaka, Japan) in an amount of 100 units/g potato starch, followed by an enzymatic reaction at pH 5.0 and 40° C. for about 18 hours to degrade α-glycosyl-L-ascorbic acids into ascorbic acid 2-glucoside and to degrade the concomitant saccharides into D-glucose. The reaction solution contained ascorbic acid 2-glucoside in a production yield of about 40%, and it contained 5-O-α-glucosyl-L-ascorbic acid and 6-O-α-glucosyl-L-ascorbic acid in a total amount of about 0.3%.

After inactivating the remaining glucoamylase by heating, the reaction solution was decolored and filtered with an activated charcoal, and the filtrate was concentrated, and fed to an anion-exchange resin (OH$^-$-form) to adsorb L-ascorbic acid and ascorbic acid 2-glucoside thereupon, followed by washing the resin with water to remove D-glucose and allowing to effect elution with 0.5 N hydrochloric acid solution. Similarly as in Example 1, the resulting eluate was fed to a simulated-moving-bed column chromatography using a strong-acid cation exchange resin to collect a fraction rich in ascorbic acid 2-glucoside but poor in L-ascorbic acid. The collected fraction contained 90.4%, d.s.b., of ascorbic acid 2-glucoside.

After being desalted with a cation-exchange resin (H$^+$-form), the fraction was concentrated in a reduced pressure into an about 75% concentrate, which was then placed in a crystallizer and admixed with the particulate composition containing ascorbic acid 2-glucoside prepared in Example 1, as a seed, in an amount of two percent of the solid contents. Thereafter, the concentrate was adjusted to 45° C. and gradually cooled to 10° C. over two days under gentle stirring conditions to crystallize ascorbic acid 2-glucoside to form anhydrous crystalline ascorbic acid 2-glucoside. The crystals were collected, washed by spraying a small amount of cold deionized water, aged and dried at 38° C. for three hours, unforcedly cooled overnight, and pulverized to obtain a particulate composition containing anhydrous crystalline ascorbic acid 2-glucoside, which had a purity of about 98.8%, contained less than 0.1% of L-ascorbic acid and D-glucose in total, contained less than 0.1% of L-ascorbic acid, had a degree of crystallinity of 93.5% for anhydrous crystalline ascorbic acid 2-glucoside, and had a total reducing power of the whole particulate composition being 0.31%. The dynamic vapor sorption level of the particulate composition was lower than detection limit. Measurement of the particle distribution of the particulate composition revealed that it contained particles with particle sizes of less than 150 μm in an amount of 93.1% and those with particle sizes of 53 μm or more but less than 150 μm in an amount of 48.2%. When subjected to the same solidification test and browning test as in Experiments 1-4 and 7, respectively, the particulate composition was judged to be "Not solidified" (−) in the solidification test and "Not browned or substantially not browned" (−) in the browning test.

The particulate composition is easily handleable because it hardly solidifies and less colors as compared to conventional "AA2G", a product name of a particulate composition containing anhydrous crystalline ascorbic acid 2-glucoside commercialized by Hayashibara Biochemical Laboratories, Inc., Okayama, Japan, in a grade for use in quasi-drugs as a skin-whitening ingredient, etc. Since the particulate composition does not differ from conventional quasi-drug-grade powders in that it is a particulate composition containing anhydrous crystalline ascorbic acid 2-glucoside, it can be used alone or in combination with other ingredients as a material for food products, cosmetics, quasi-drugs, pharmaceuticals, etc., similarly as the above conventional powders. Since the particulate composition has an L-ascorbic acid content of 0.1% or lower, the particulate composition per se is free of fear of causing coloration even when stored for a relatively long period of time in the same product form as conventional powders in a grade for quasi-drugs. Since the particulate composition has an L-ascorbic acid content of 0.1% or lower, there is no fear of causing coloration in the particulate composition per se even when the composition is stored for a relatively long period of time in the same product form as conventional quasi-drug-grade powders.

EXAMPLE 4

Preparation of Particulate Composition Containing Anhydrous Crystalline Ascorbic Acid 2-Glucoside An enzymatic reaction was carried out by the method similarly as in Example 3 except for allowing 500 units/g solid of starch of isoamylase (produced by Hayashibara Co., Ltd., Okayama, Japan) to act on the starch at 55° C. together with the CGTase. After glucoamylase treatment, the reaction solution contained ascorbic acid 2-glucoside in a production yield of about 45%. The reaction solution contained 5-O-α-glucosyl-L-ascorbic acid and 6-O-α-glucosyl-L-ascorbic acid in a total amount of about 0.2%. The reaction solution was purified similarly as in Example 3 to collect a fraction with an ascorbic acid 2-glucoside content of 91.8%, d.s.b.

After crystallization conducted similarly as in Example 3, the resulting crystals were collected, washed by spraying a small amount of cold deionized water, aged and dried at 38° C. for three hours, unforcedly cooled overnight, and pulverized to obtain a particulate composition containing anhydrous crystalline ascorbic acid 2-glucoside, which had a purity of 99.2%, contained less than 0.1% of L-ascorbic acid and D-glucose in total, contained less than 0.1% of L-ascorbic acid, had a degree of crystallinity of 95.6% for anhydrous crystalline ascorbic acid 2-glucoside, and had a total reducing power of 0.25%. The dynamic vapor sorption level of the particulate composition was lower than detection limit. Measurement of the particle distribution of the particulate composition revealed that it contained particles with particle sizes of less than 150 μm in an amount of 92.7% and those with particle sizes of 53 μm or more but less than 150 μm in an amount of 44.2%. When subjected to the same solidification test and browning test as in Experiments 1-4 and 7, respectively, the particulate composition was judged to be "Not solidified" (−) in the solidification test and "Not browned or substantially not browned" (−) in the browning test.

The particulate composition is easily handleable because it hardly solidifies and less colors as compared to conventional "AA2G", a product name of a particulate composition containing anhydrous crystalline ascorbic acid 2-glucoside commercialized by Hayashibara Biochemical Laboratories, Inc., Okayama, Japan, in a grade for use in quasi-drugs as a skin-whitening ingredient, etc. Since the particulate composition does not differ from conventional quasi-drug-grade powders in that it is a particulate composition containing anhydrous crystalline ascorbic acid 2-glucoside, it can be used alone or in combination with other ingredients as a material for food products, cosmetics, quasi-drugs, pharmaceuticals, etc., similarly as the above conventional powders. Since the particulate composition has an L-ascorbic acid content of 0.1% or lower, there is no fear of causing coloration in the particulate composition per se even when the composition is stored for a relatively long period of time in the same product form as conventional quasi-drug-grade powders.

EXAMPLE 5

Preparation of Particulate Composition Containing Anhydrous Crystalline Ascorbic Acid 2-Glucoside Five parts by weight of potato starch was added to 15 parts by weight of water and then dissolved therein by heating after the addition of a commercialized starch-liquefying enzyme. The solution was admixed with three parts by weight of L-ascorbic acid and adjusted to pH 5.5 to give a substrate solution. The substrate solution was admixed with CGTase (produced by Hayashibara Biochemical Laboratories, Inc., Okayama, Japan, derived from *Geobacillus stearothermophilus* Tc-91 strain (deposited under the accession number of FERM P-2225 and under transferring to International Deposit under the accession number of FERM ABP-11273 in International Patent Organism Depositary in National Institute of Advanced Industrial Science and Technology) and isoamylase (produced by Hayashibara Biochemical Laboratories, Inc., Okayama, Japan) in respective amounts of 100 units and 1,000 units per gram of the potato starch and reacted at 55° C. for 50 hours to form ascorbic acid 2-glucoside and other α-glycosyl-L-ascorbic acids. After inactivating the enzymes by heating, the reaction solution was adjusted to pH 4.5, admixed with "GLUCOZYME #20000", a product name of a glucoamylase with an activity of 20,000 units/g, commercialized by Nagase ChemteX Corp., Osaka, Japan, by 50 units per gram of the potato starch, reacted at 55° C. for 24 hours to degrade α-glycosyl-L-ascorbic acids into ascorbic acid 2-glucoside and to degrade the concomitant saccharides into D-glucose. The production yield of ascorbic acid 2-glucoside was about 38%, d.s.b. The reaction solution contained 5-O-α-glucosyl-L-ascorbic acid and 6-O-α-glucosyl-L-ascorbic acid in a total amount of about 0.4%, d.s.b.

After inactivating the enzyme by heating, the reaction solution was decolored and filtered with an activated charcoal. The filtrate was desalted with a cation-exchange resin ($H^+$-form) and subjected to an anion-exchange resin ($OH^-$-form) to adsorb L-ascorbic acid and ascorbic acid 2-glucoside thereupon, followed by washing the resin with water to remove D-glucose and eluting the adsorbed ingredients with 0.5 N hydrochloric acid. The eluent was fed to column chromatography using "TOYOPEARL HW-40", a product name of a porous resin of Tosoh Corp., Tokyo, Japan, to collect a fraction rich in ascorbic acid 2-glucoside but poor in L-ascorbic acid. The collected fraction contained ascorbic acid 2-glucoside in an amount of 87.6%, d.s.b.

After the fraction was concentrated in a reduced pressure to give a concentration of about 76%, the concentrate was placed in a crystallizer, admixed with the particulate composition containing anhydrous crystalline ascorbic acid 2-glucoside prepared in Example 1, as a seed, in an amount of two percent of the solid contents, adjusted to 40° C., gradually cooled to 15° C. over two days under gently stirring conditions to crystallize ascorbic acid 2-glucoside to form anhydrous crystalline ascorbic acid 2-glucoside. The crystals were collected with a basket-type centrifuge, washed by spraying a small amount of distilled water, aged and dried at 35° C. for eight hours, cooled by blowing 20° C. air for 10 minutes, and pulverized to obtain a particulate composition containing anhydrous crystalline ascorbic acid 2-glucoside. The particulate composition had a purity of 98.5% for ascorbic acid 2-glucoside, contained less than 0.1% of L-ascorbic acid and D-glucose in total, contained less than 0.1% of L-ascorbic acid, had a degree of crystallinity of 94.8% for anhydrous crystalline ascorbic acid 2-glucoside, and had a total reducing power of the whole particulate composition being 0.15%. The dynamic vapor sorption level of the particulate composition was lower than detection limit. Measurement of the particle distribution of the particulate composition revealed that it contained particles with particle sizes of less than 150 μm in an amount of 83.0% and those with particle sizes of 53 μm or more but less than 150 μm in an amount of 57.7%. When subjected to the same solidification test and browning test as in Experiments 1-4 and 7, respectively, the particulate composition was judged to be "Not solidified" (−) in the solidification test and "Not browned or substantially not browned" (−) in the browning test.

The particulate composition is easily handleable because it hardly solidifies and less colors as compared to conventional "AA2G", a product name of a particulate composition containing anhydrous crystalline ascorbic acid 2-glucoside commercialized by Hayashibara Biochemical Laboratories, Inc., Okayama, Japan, in a grade for use in quasi-drugs as a skin-whitening ingredient, etc. Since the particulate composition does not differ from conventional quasi-drug-grade powders in that it is a particulate composition containing anhydrous crystalline ascorbic acid 2-glucoside, it can be used alone or in combination with other ingredients as a material for food products, cosmetics, quasi-drugs, pharmaceuticals, etc., similarly as the above conventional powders. Since the particulate composition has an L-ascorbic acid content of 0.1% or lower, there is no fear of causing coloration in the particulate composition per se even when the composition is stored for a relatively long period of time in the same product form as conventional quasi-drug-grade powders.

COMPARATIVE EXAMPLE 1

Preparation of Particulate Composition Containing Anhydrous Crystalline Ascorbic Acid 2-Glucoside Except for not using isoamylase, a particulate composition containing anhydrous crystalline ascorbic acid 2-glucoside was prepared by the same method as in Example 5 using CGTase from *Geobacillus stearothermophilus* Tc-91 strain (deposited under the accession number of FERM P-2225 and under transferring procedure to International Deposit under the accession number of ABP-11273 in International Patent Organism Depositary in National Institute of Advanced Industrial Science and Technology) produced by Hayashibara Biochemical Laboratories, Inc., Okayama, Japan. The production yield of ascorbic acid 2-glucoside after glucoamylase treatment was about 28%. The reaction solution contained 5-O-α-glucosyl L-ascorbic acid and 6-O-α-glucosyl L-ascorbic acid in a total amount of about 1.0%, d.s.b. Similarly as in Example 5, the reaction solution was decolored, desalted, and purified to collect a fraction rich in ascorbic acid 2-glucoside. The collected fraction contained ascorbic acid 2-glucoside in an amount of 87.7%, d.s.b.

Similarly as in Example 5, the fraction rich in ascorbic acid 2-glucoside was concentrated to crystallize ascorbic acid 2-glucoside, and the resulting crystals were collected, aged, dried, and cooled to obtain a particulate composition containing anhydrous crystalline ascorbic acid 2-glucoside had, which had a purity of 98.5% for ascorbic acid 2-glucoside, contained 0.4% of L-ascorbic acid and D-glucose in total, contained 0.2% of L-ascorbic acid, had a degree of crystallinity of 89.1% for anhydrous crystalline ascorbic acid 2-glucoside, and had a total reducing power of the whole particulate composition being 1.17%. The dynamic vapor sorption level of the particulate composition was 0.04%. Measurement of the particle distribution of the particulate composition revealed that it contained particles with a particle size of less than 150 μm in an amount of 78.1% and those with a particle size of 53 μm or more but less than 150 μm in an amount of 50.2%.

When subjected to the same solidification test and browning test as in Experiments 1-4 and 7, respectively, the particulate composition was judged to be "Solidified" (+) in the solidification test and "Browned" (+) in the browning test. Since the particulate composition has a degree of crystallinity of less than 90% for anhydrous crystalline ascorbic acid 2-glucoside and a dynamic vapor sorption level of 0.04% as being over 0.01%, it may cause solidification during its distribution and storing period of time and this would inevitably cause serious problems when used as a material for food products, cosmetics, quasi-drugs, pharmaceuticals, etc. Since the particulate composition contains L-ascorbic acid as high as 0.2%, it in itself is free of fear of causing coloration during commercial distribution and storage period of time.

Since the particulate composition has an L-ascorbic acid content of as high as 0.2%, there is fear of causing coloration in the particulate composition per se during commercial distribution and storage period of time.

<Test for Storage Stability>

The particulate compositions containing anhydrous crystalline ascorbic acid 2-glucoside obtained in Examples 1 to 5 and Comparative Example 1, were tested for their storage stabilities by the same method as in Experiment 5-3. The results in this experiment and those of the solidification tests confirmed in Examples and Comparative Example are shown in Table 8 in parallel.

TABLE 8

| Test sample No. | Storage stability | Solidification |
| --- | --- | --- |
| Example 1 | − | − |
| Example 2 | − | − |
| Example 3 | − | − |
| Example 4 | − | − |
| Example 5 | − | − |
| Comparative Example 1 | + | + |

As shown in Table 8, in the storage stability test, in which each test sample was stored under a condition packed in a 10-kg bag for 45 days according to an actually-commercialized-product form, any of the particulate compositions containing anhydrous crystalline ascorbic acid 2-glucoside of Examples 1 to 5 was judged to be "Not solidified" (−), but the particulate composition containing anhydrous crystalline ascorbic acid 2-glucoside of Comparative Example 1 was judged to be "Solidified" (+). These results were well coincided with those in the solidification test.

As described above, the particulate compositions containing anhydrous crystalline ascorbic acid 2-glucoside of the present invention, as shown in Experiments 1 to 7 and Examples 1 to 5, have a degree of crystallinity of 90% or higher for anhydrous crystalline ascorbic acid 2-glucoside or have a dynamic vapor sorption level of 0.01% or lower, and therefore, they are so handleable particulate compositions as to be judged "Not solidified" (−) in the solidification test, even though, while they contain L-ascorbic acid and/or D-glucose as impurities characteristic to their production processes in a detectable level by conventional liquid chromatography, the purities of ascorbic acid 2-glucoside in the particulate compositions are of over 98.0% but less than 99.9%, specifically, 98.5% or over (see Example 5) but 99.8% or lower (see Experiment 2), which is the level less than 99.9% of ascorbic acid 2-glucoside in the reagent grade powder and making distinguishable the particulate compositions of the present invention from the reagent grade powder in terms of the purity of ascorbic acid 2-glucoside.

EXAMPLE 6

Powdered Preparation of Vitamin C (Application Example as a Food Material)

Twenty parts by weight of a particulate composition containing anhydrous crystalline ascorbic acid 2-glucoside obtained by any of the methods in Examples 1 to 5 for use as a powderous material for food products, was admixed with 70 parts by weight of sucrose, 10 parts by weight of dextrin, and an adequate amount of a flavor, followed by mixing the resulting mixture by a mixer into a powdered preparation of vitamin C. The product can be prepared by easily mixing to homogeneity a particulate composition containing anhydrous crystalline ascorbic acid 2-glucoside with other powder by using a mixer without causing any troublesome event during its preparation step. The product can be easily mixed with other materials for food products and it is a powdered preparation of vitamin C substantially free from causing coloration or solidification even when stored for a relatively long period of time. Since the product and compositions containing the same have the physiological functions of vitamin C, they can be orally taken to maintain the health or the whitening of the skin or the mucosae.

EXAMPLE 7

Skin-whitening Powder (Application Example as a Cosmetic Material)

<Formulation>

| (Ingredients) | (%) |
|---|---|
| α,α-Trehalose | 59.5 |
| Polyethylene glycol 6000 | 20 |
| Silica | 5 |
| Particulate composition containing anhydrous crystalline ascorbic acid 2-glucoside obtained by any of the methods of Examples 1 to 5 | 15 |
| Flavor | Adequate amount |
| Color | Adequate amount |
| Antiseptic | Adequate amount |
| Voluming up to 100%. | |

<Preparation Method>

The above α,α-trehalose, polyethylene glycol 6000, silica, flavor, color, and antiseptic were placed in and mixed to homogeneity with a mixer into a powdered mixture. To the mixture was added the particulate composition containing anhydrous crystalline ascorbic acid 2-glucoside obtained in any of the methods in Examples 1 to 5, followed by stirring and mixing the mixture to homogeneity to obtain a skin-whitening powder. The product facilitates to mix a particulate composition containing anhydrous crystalline ascorbic acid 2-glucoside with other ingredients into a homogeneous mixture by using a mixer, without causing any troublesome event during its preparation step. Since the product can be easily mixed with other materials for cosmetics and it is a skin-whitening powder substantially free from causing coloration or solidification even when stored for a relatively long period of time. The product and compositions containing the same can be used as an external dermatological agent for skin whitening.

As described above, since the particulate composition containing anhydrous crystalline ascorbic acid 2-glucoside of the present invention is significantly, hardly solidifiable compared to conventionally commercialized quasi-drug-grade powders as materials for cosmetics, quasi-drugs, and food products, the particulate composition has the merit that it is readily handleable and substantially free from losing its satisfactory free-flowing ability as a particulate composition during its storage, preservation, or transportation. In spite of the fact that the particulate composition containing anhydrous crystalline 2-glucoside of the present invention is significantly, hardly solidifiable compared to conventional quasi-drug-grade powders, it is not necessary to increase its purity of ascorbic acid 2-glucoside to the level of reagent grade powders and, therefore, there is no need for additional steps in the production process such as recrystallization and/or repetition of washing crystals. Because of this, the particulate composition of the present invention has the advantage that the production yield does not decrease by a large margin and it can be produced at a lesser cost.

According to the process of the present invention, the particulate composition of the present invention can be produced from L-ascorbic acid and amylaceous substance as materials by the production process which does not differ from the production process for producing conventional quasi-drug-grade powders in the steps comprised therein. Therefore, the production process of the present invention has the advantageous merit that it produces a significantly, hardly solidifiable particulate composition containing anhydrous crystalline ascorbic acid 2-glucoside compared with the conventional quasi-drug-grade powders, with substantially the same period of time, labor, production-facilities, and cost as those required for producing such conventional powders.

According to the powderous materials for food products, cosmetics, quasi-drugs, and pharmaceuticals of the present invention, because they consist of the particulate composition having the significantly, hardly solidifiable property, the following advantageous merit can be obtained: There is no fear of causing disturbance during material transportation, sieving, and mixing even when used in production plants that are so designed, on the premises, as to use materials having satisfactory free-flowing ability.

Further, since the particulate composition containing anhydrous crystalline ascorbic acid 2-glucoside of the present invention can be easily prepared into the one having both particles with a particle size of less than 150 μm in an amount of 70% by weight or more to the whole particulate composition and those with a particle size of at least 53 μm but less than 150 μm in an amount of 40 to 60% by weight, it can be used conventionally without altering conventional production steps and material standards even when used as materials for food products, cosmetics, quasi-drugs, and pharmaceuticals. When the particulate composition containing anhydrous crystalline ascorbic acid 2-glucoside of the present invention is of the one which contains L-ascorbic acid and/or D-glucose and has a reducing power of the whole particulate composition being less than one percent, it attains the merit that, although it is a particulate composition produced from L-ascorbic acid and amylaceous substance as materials, it is free of fear of causing quality deterioration such as browning even when mixed with other ingredients having amino group intramolecularly, such as amino acids and proteins. In particular, when the content of L-ascorbic acid in the particulate composition containing anhydrous crystalline ascorbic acid 2-glucoside of the present invention is 0.1% by weight of lower, d.s.b., the particulate composition per se is free of fear of being discolored with pale brown color even when stored alone for a relatively long period of time, and it can be used as a substantially uncolored, white powderous material for foods, cosmetics, quasi-drugs, and pharmaceuticals.

Further, since the particulate composition containing anhydrous crystalline ascorbic acid 2-glucoside of the present invention is significantly hardly solidifiable compared to conventional quasi-drug-grade powders, it can be more easily handleable than the conventional ones and used as a material for food products, cosmetics, quasi-drugs, or pharmaceuticals in the fields of food products, cosmetics, quasi-drugs, pharmaceuticals, feeds, baits, chemical products, and industrial products. The production method of the particulate composition containing anhydrous crystalline ascorbic acid 2-glucoside of the present invention can be used as a method of producing the same from amylaceous substances and L-ascorbic acid, as natural materials, in a desired amount and at a lesser cost in the fields of producing starch-saccharified products or vitamin derivatives.

While there has been described what is at present considered to be the preferred embodiments of the invention, it will be understood the various modifications may be made therein, and it is intended to cover in the appended claims all such modifications as fall within the true spirits and scope of the invention.

The invention claimed is:

1. A process for producing a particulate composition comprising anhydrous crystalline 2-O-α-D-glucosyl-L- ascorbic acid;
wherein said particulate composition comprises 2-O-α-D-glucosyl-L- ascorbic acid in an amount of over 98.0% by weight but less than 99.9% by weight, on a dry solid basis; and has a degree of crystallinity of 90% or higher for anhydrous crystalline 2-O-α-D-glucosyl-L-ascorbic acid, when calculated based on a profile of powder X-ray diffraction analysis of said particulate composition,
said process comprising the steps of:
(a) allowing cyclomaltodextrin glucanotransferase and glucoamylase in this order to act on a solution comprising amylaceous substance and L-ascorbic acid to obtain a solution comprising 2-O-α-D-glucosyl-L-ascorbic acid in a production yield of 35% by weight or higher of 2-O-α-D-glucosyl-L-ascorbic acid;
(b) purifying the resulting solution to increase the content of 2-O-α-D-glucosyl-L-ascorbic acid to a level of over 86% by weight, on a dry solid basis;
(c) crystallizing anhydrous crystalline 2-O-α-D- glucosyl-L-ascorbic acid from the resulting purified solution;
(d) collecting the resulting precipitated anhydrous crystalline 2-O-α-D-glucosyl-L-ascorbic acid without any re-crystallizing step; and
(e) ageing and drying the collected anhydrous crystalline 2-O-α-D-glucosyl-L-ascorbic acid; and
said cyclomaltodextrin glucanotransferase is from *Geobacillus stearothermophilus* Tc-62 or Tc-27, or a mutant cyclomaltodextrin glucanotransferase of *Geobacillus stearothermophilus* Tc-91, having an amino acid sequence that the 228th lysine residue in the amino acid sequence of SEQ ID NO:1 is replaced with glutamic acid residue.

2. The process of claim 1, wherein in the step (a), said cyclomaltodextrin glucanotransferase is allowed to act on the solution in combination with a starch-debranching enzyme.

3. The process of claim 1, wherein, the step (b) contains a step of removing saccharides by column chromatography using an anion-exchange resin, and simulated-moving-bed column chromatography using a cation-exchange resin as a packing material.

4. The process of claim 1, wherein the step (b) contains a step of removing saccharides by column chromatography using an anion-exchange resin, and column chromatography using a strong-acid cation-exchange resin or a porous resin.

5. The process of claim 1 wherein the dried product of step (e) is pulverized.

* * * * *